United States Patent
Dharwad et al.

(10) Patent No.: US 11,496,232 B1
(45) Date of Patent: Nov. 8, 2022

(54) WAVEFORM SYNCHRONIZATION SYSTEM FOR DATA RECEIVED FROM A NETWORK

(71) Applicant: Nihon Kohden Digital Health Solutions, Inc., Irvine, CA (US)

(72) Inventors: Harsh Dharwad, San Diego, CA (US); Timothy Ruchti, Gurnee (CA); Paul Hughes, Phoenix, AZ (US); Abel Lin, San Diego, CA (US)

(73) Assignee: Nihon Kohden Digital Health Solutions, Inc., Irvine, CA (US)

( * ) Notice: Subject to any disclaimer, the term of this patent is extended or adjusted under 35 U.S.C. 154(b) by 0 days.

(21) Appl. No.: 17/306,864

(22) Filed: May 3, 2021

(51) Int. Cl.
    *H04L 12/26* (2006.01)
    *H04J 3/06* (2006.01)
    *H04L 69/16* (2022.01)
    *A61B 5/024* (2006.01)
    *H04L 47/34* (2022.01)
    *H04L 67/12* (2022.01)

(52) U.S. Cl.
    CPC ........ *H04J 3/0661* (2013.01); *A61B 5/02405* (2013.01); *H04L 47/34* (2013.01); *H04L 69/16* (2013.01); *H04L 67/12* (2013.01)

(58) Field of Classification Search
    None
    See application file for complete search history.

(56) References Cited

U.S. PATENT DOCUMENTS

| | | | |
|---|---|---|---|
| 5,708,432 A | 1/1998 | Reynolds et al. | |
| 6,522,706 B1* | 2/2003 | Bahai | H04B 1/7073 375/357 |
| 7,788,110 B2* | 8/2010 | Ogino | G16H 40/20 705/2 |
| 8,024,030 B2* | 9/2011 | Douglas | A61B 5/366 600/517 |

(Continued)

OTHER PUBLICATIONS

International Search Report and Written Opinion issued in PCT/US2022/027342 dated Aug. 8, 2022 (11 pages).

(Continued)

*Primary Examiner* — Sithu Ko
(74) *Attorney, Agent, or Firm* — Arc IP Law, PC; Joseph J. Mayo

(57) ABSTRACT

A system that synchronizes waveforms received over a network from one or more devices, such as medical devices. Because of network delays or losses, waveforms can arrive at varying rates and times. Precise post-synchronization of the received data, to within a few milliseconds, is needed for accurate analysis. Applications include automatic classification of waveforms, such as detection of myocardial infraction from heart monitor waveforms. Synchronization uses sequence numbers assigned by each device, but must also account for sequence number wraparounds. Waveforms may also be synchronized across devices, by calculating the bias between within-device synchronized times and a common time source or common disturbance. Waveform data may also be stored data in a database or data warehouse; embodiments may index the data using a key with a date-time prefix (Continued)

and a hash code suffix, to support distributed indexing while reducing the chance of hash collisions to a very small probability.

20 Claims, 17 Drawing Sheets

(56) References Cited

U.S. PATENT DOCUMENTS

| | | | | |
|---|---|---|---|---|
| 8,180,440 | B2* | 5/2012 | McCombie | A61B 5/0205 |
| | | | | 600/513 |
| 8,594,776 | B2* | 11/2013 | McCombie | A61B 5/1123 |
| | | | | 600/595 |
| 8,684,942 | B2* | 4/2014 | Zhang | A61B 5/352 |
| | | | | 600/508 |
| 8,825,148 | B2* | 9/2014 | Zhang | A61B 5/352 |
| | | | | 600/523 |
| 9,219,600 | B1* | 12/2015 | Landon | H04L 7/0331 |
| 9,486,148 | B2* | 11/2016 | Hseu | A61B 5/318 |
| 9,565,633 | B2* | 2/2017 | Samardzija | H04W 4/80 |
| 10,356,001 | B1* | 7/2019 | Drakulic | A61B 5/308 |
| 2005/0249323 | A1 | 11/2005 | Konz | |
| 2007/0087734 | A1* | 4/2007 | Hinterberger | G04R 20/02 |
| | | | | 455/418 |
| 2008/0218382 | A1 | 9/2008 | Kavaler | |
| 2009/0131762 | A1 | 5/2009 | Pelzek et al. | |
| 2010/0298654 | A1* | 11/2010 | McCombie | A61B 5/282 |
| | | | | 600/595 |
| 2013/0070777 | A1 | 3/2013 | Hutchison et al. | |
| 2017/0249445 | A1* | 8/2017 | Devries | A61B 5/742 |
| 2019/0379408 | A1* | 12/2019 | Ma | H04L 7/0025 |

OTHER PUBLICATIONS

Matsuda, et al., "Onboard software of plasma wave experiment aboard ARASE: Instrument management and signal processing of waveform capture/onboard frequency analyzer" Earth, Planets and Space 70.1 (2018) 1-22.

* cited by examiner

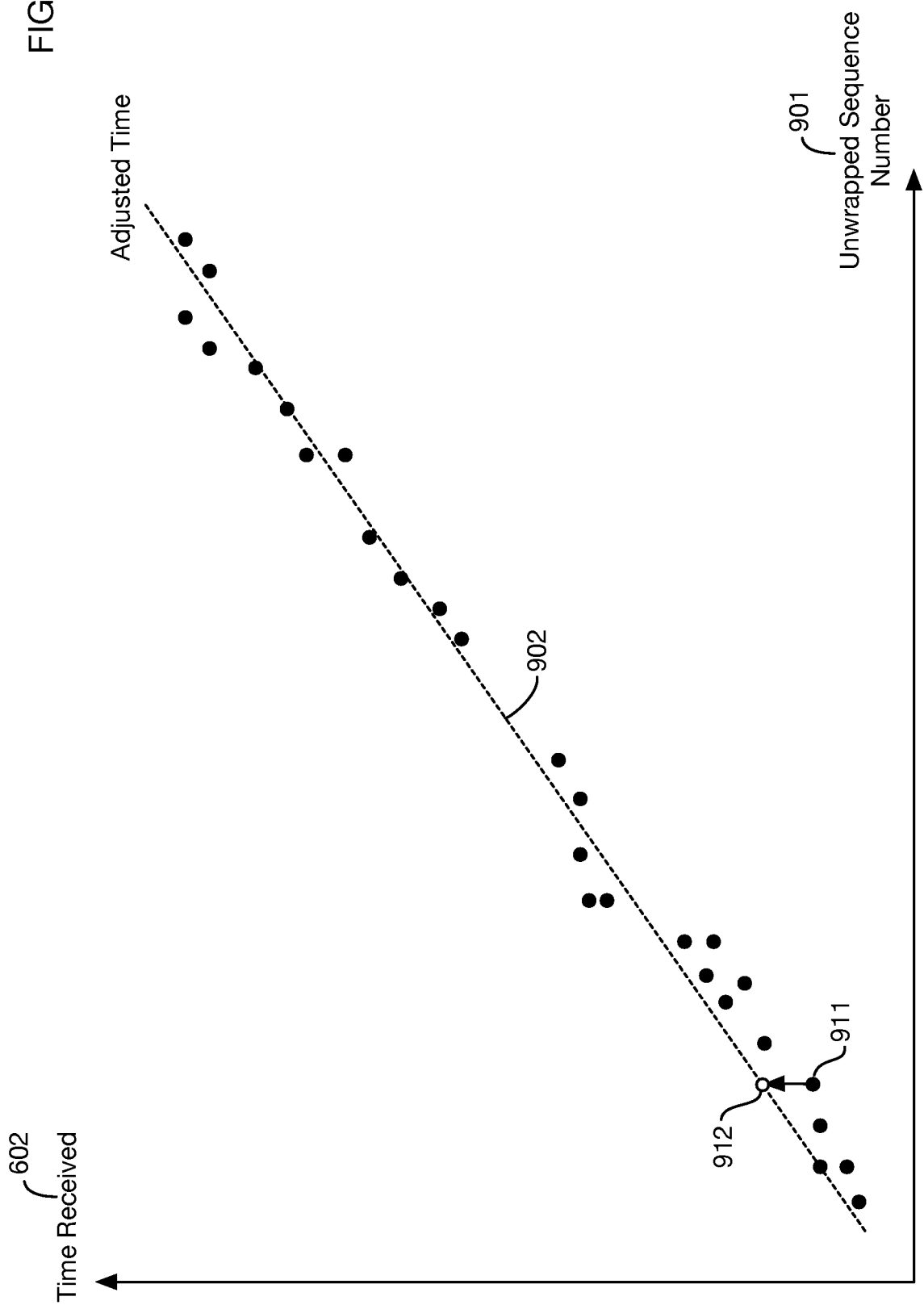

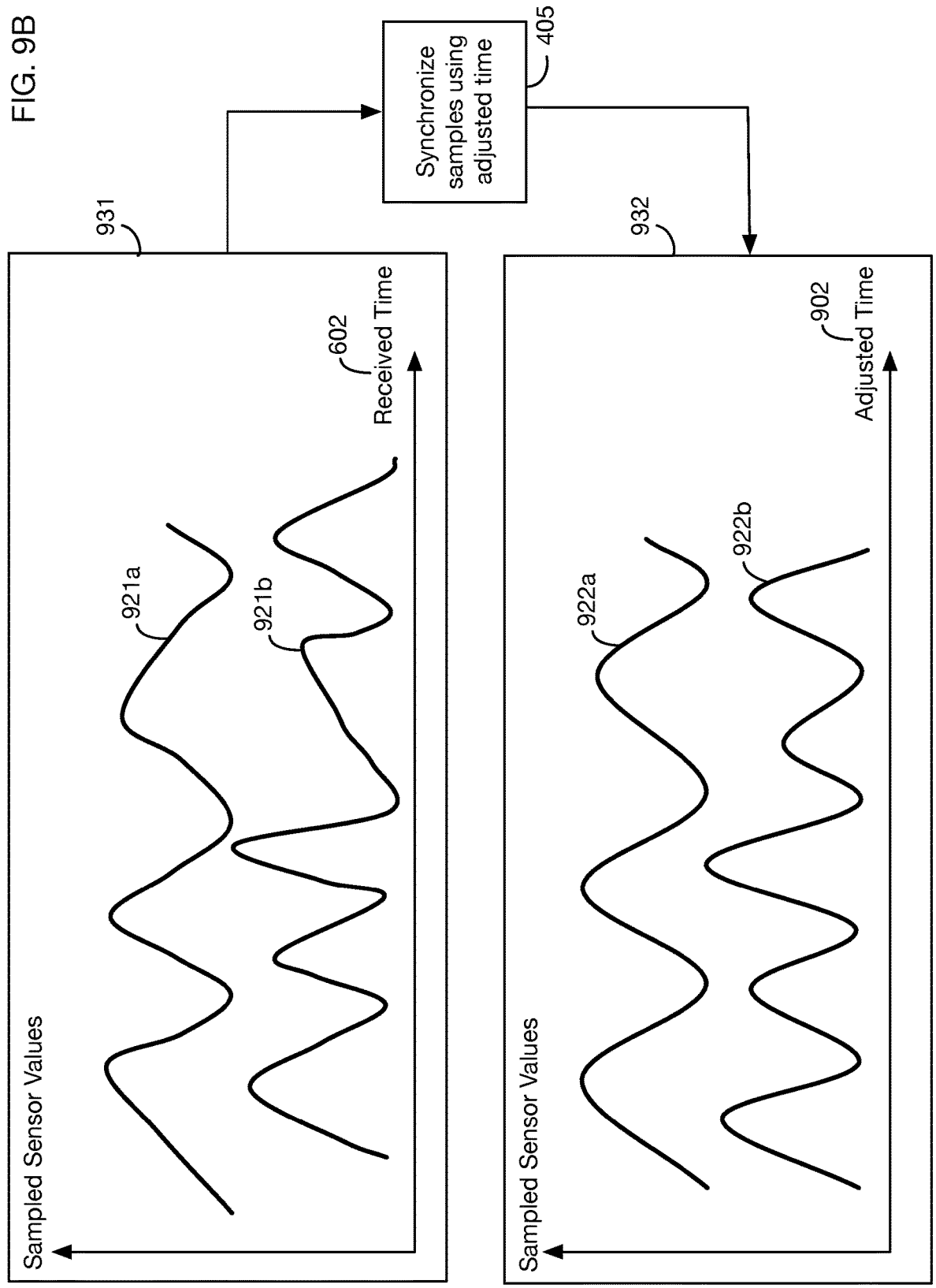

FIG. 11
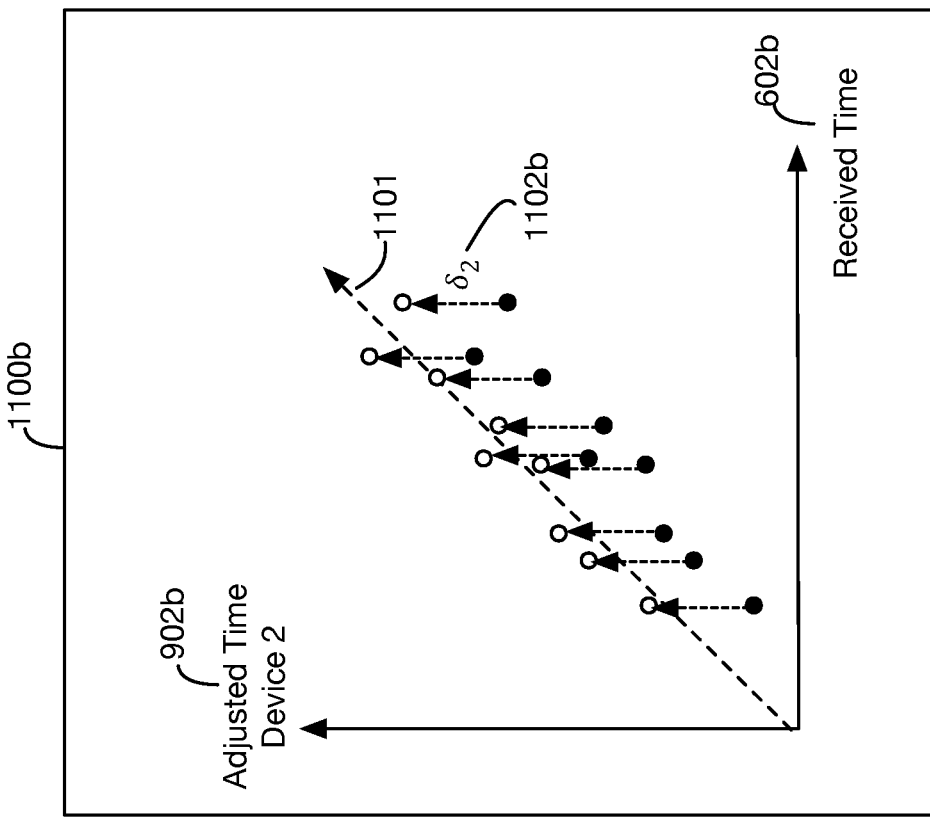
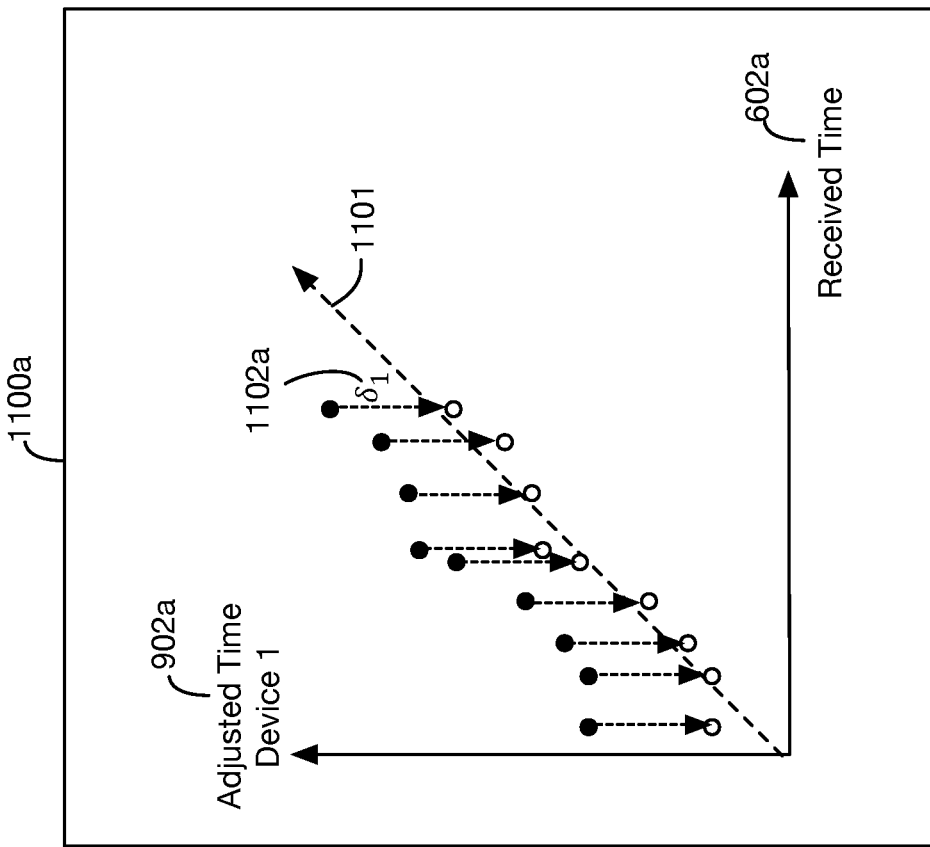

WAVEFORM SYNCHRONIZATION SYSTEM FOR DATA RECEIVED FROM A NETWORK

BACKGROUND OF THE INVENTION

Field of the Invention

One or more embodiments of the invention are related to the fields of information systems and medical devices. More particularly, but not by way of limitation, one or more embodiments of the invention enable a waveform synchronization system for data received from a network.

Description of the Related Art

Network-enabled sensing devices are increasingly available, and offer the potential for collection and automated analysis of data streamed from these devices. In the medical field, for example, patient monitors may collect massive amounts of data at the bedside, and transmit this data to servers for analysis. The network connections between devices and servers can introduce significant and variable latencies between transmission and receipt. These latencies can cause data received from multiple sensors, either within or across devices, to drift out of synchronization. Accurate analysis may require that waveform data be synchronized after receipt to within a small number of milliseconds. There are no known systems that can achieve this degree of precise synchronization on data transmitted over networks.

For at least the limitations described above there is a need for a waveform synchronization system for data received from a network.

BRIEF SUMMARY OF THE INVENTION

One or more embodiments described in the specification are related to a waveform synchronization system for data received from a network. Embodiments of the invention may synchronize waveform data from devices, both within and across devices, to correct for time skews introduced by network transmission latencies and clock inconsistencies among devices.

One or more embodiments may have one or more processors connected to a network that is also connected to one or more devices. Each device may repeatedly sample data from one or more sensors over a time interval. The time interval may have multiple sampling cycles, each with a cycle duration approximately equal to the same sampling period. A device may assign a sequence number to each sampling cycle. This number may be within a range between a minimum and maximum. Sequence numbers may be incremented at each successive cycle, but when the maximum value is incremented the sequence number may rollover to the minimum value. The sequence number period is the number of distinct sequence numbers between the minimum and maximum.

A device may transmit over the network one or more packets for each sampling cycle. Each packet may contain the sequence number and data from one or more of the device's sensors. One or more receiving processors may receive the packets and add a received timestamp, to form augmented packets. The network may delay transmission of any of the packets, reorder the packets, or lose any of the packets. One or more synchronizing processors may receive the augmented packets. To synchronize these augmented packets, the synchronizing processor(s) may unwrap the sequence numbers to form unwrapped sequence numbers that uniquely identify each sampling cycle. They may then calculate a linear relationship between the unwrapped sequence numbers and the received timestamps, and apply this relationship to obtain an adjusted timestamp for each augmented packet. The packets may then be synchronized to form synchronized waveforms based on their adjusted timestamps.

In one or more embodiments, one or more of the devices may be medical devices, such as a heart monitor with sensors corresponding to the heart monitor leads.

In one or more embodiments, devices may transmit data over the network using the User Datagram Protocol.

In one or more embodiments, each sequence number may have an associated bit length, and the sequence numbers may range between 0 and two raised to the power of the bit width, minus one. The sequence number period may be two raised to the power of the bit width.

In one or more embodiments, calculation of unwrapped sequence numbers may calculate a linear mapping from received timestamps to predicted approximate unwrapped sequence numbers. The unwrapped sequence number may then be calculated as the number differing from the sequence number by an integral multiple of the sequence period, which is closest to the linear mapping applied to the received timestamp of the associated packet.

In one or more embodiments, the linear relationship between unwrapped sequence numbers and received timestamps may be calculated as a linear regression between received timestamps and unwrapped sequence numbers for the augmented packets for all of the sampling cycles.

In one or more embodiments, the linear relationship between unwrapped sequence numbers and received timestamps may be calculated as the line through the received timestamp and unwrapped sequence number of the augmented packet having the lowest received timestamp. The line may also pass through the received timestamp and unwrapped sequence number of the augmented packet having the highest received timestamp, or it may be the line with slope equal to the sampling period.

In one or more embodiments, one or more inter-device synchronizing processors may synchronize within-device synchronized waveform data across two (or more) devices. Inter-device synchronization may calculate an adjusted time bias for each device, which equals the average difference between the adjusted time and received time for the augmented packets of the device. The bias may be subtracted from the adjusted time for each device's data to synchronize the devices.

In one or more embodiments, inter-device synchronization may calculate a cross-correlation at a series of time offsets between synchronized data of one device and synchronized data of another device that is offset in time by each time offset. The phase offset may be determined as the time offset corresponding to the maximum cross-correlation. The phase offset may be subtracted from the adjusted timestamp of the data for the second device to synchronize the devices.

One or more embodiments may contain a database and one or more data storage processors that calculate an index for each augmented packet, and save the index and augmented packet data in the database. The index may be calculated by calculating a date-time prefix based on the adjusted timestamp of the augmented packet, and calculating a hash code based on or more fields of the augmented packet, and concatenating the date-time prefix and the hash code. The date-time prefix may be for example all or a portion of a POSIX time code.

BRIEF DESCRIPTION OF THE DRAWINGS

The above and other aspects, features and advantages of the invention will be more apparent from the following more particular description thereof, presented in conjunction with the following drawings wherein:

FIG. 9A illustrates a method that may be used to map unwrapped sequence number to an adjusted time that can be used to synchronize waveforms.

FIG. 9B shows use of the adjusted time to synchronize waveforms.

FIG. 11 illustrates one method that may be used to synchronize waveforms across devices, which adjusts times so that the average adjusted time equals the average received time.

DETAILED DESCRIPTION OF THE INVENTION

A waveform synchronization system for data received from a network will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
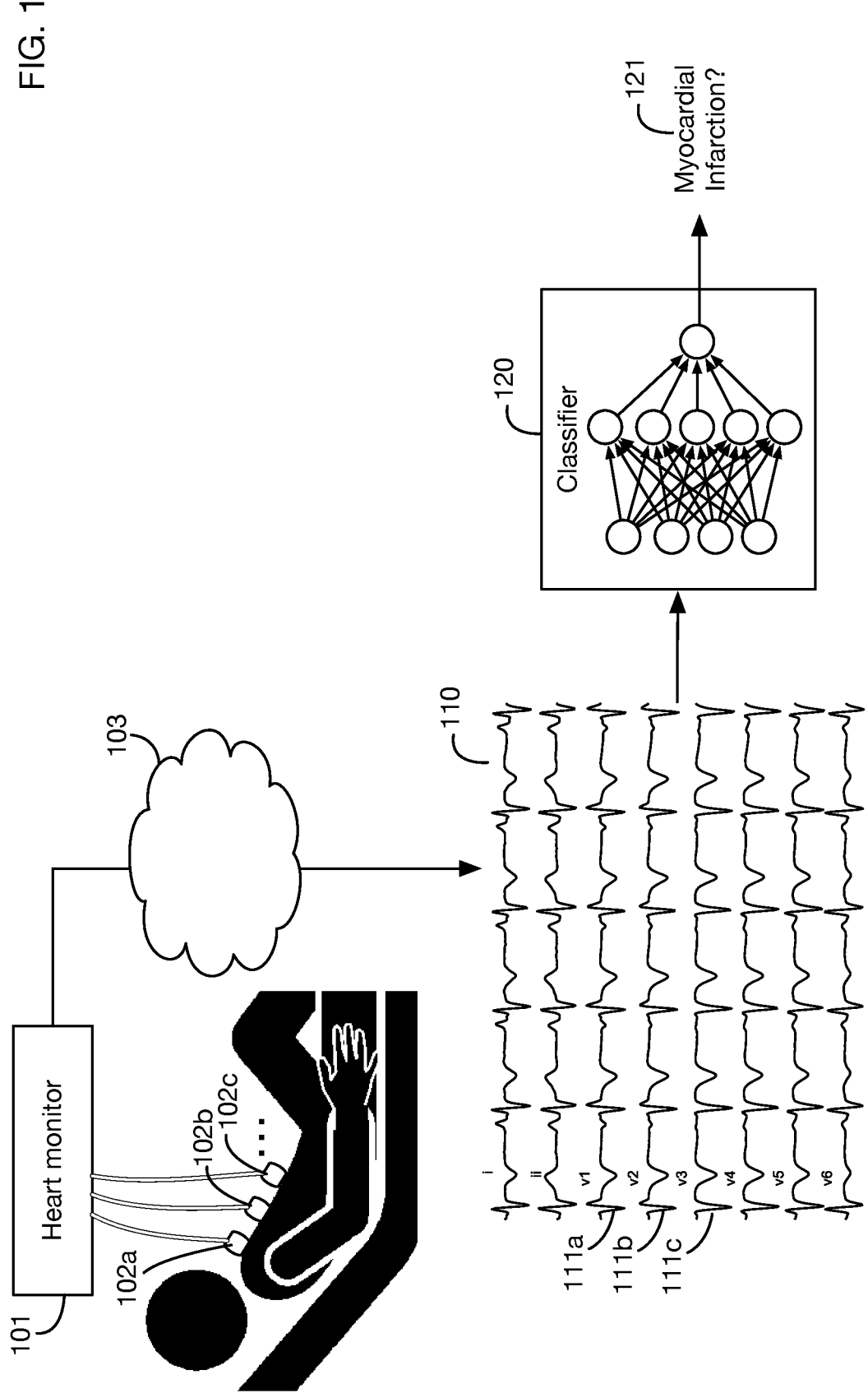
FIG. 1 shows an illustrative problem addressed by one or more embodiments of the invention: multiple waveforms are captured from a device such as a heart rate monitor, and these waveforms are input into a classifier to determine whether an event such as a myocardial infarction has occurred.

Waveform data requires time phase alignment at millisecond accuracy to be suitable for data analysis. An illustrative analysis of waveforms from a multi-channel heart monitor 101 is shown in FIG. 1. Heart monitor 101 collects data from the sensor attached to the patient; three illustrative sensors 102a, 102b, and 102c are shown. The heart monitor itself may for example be at the patient's bedside. Waveform data 110 may be transmitted from heart monitor 101 to one or more other systems for analysis, over a network or networks 103. The system or systems that analyze waveform data may for example be hospital servers, cloud-based resources, or any type of processor or processors. Data may be transmitted in a live stream from the heart monitor so that analysis can be performed soon after data arrives. Waveform data 110 contains for example waveform 111a corresponding to readings from sensor 102a, waveform 111b corresponding to readings from sensor 102b, and waveform 111c corresponding to readings from sensor 102c. Waveforms 110 may for example be analyzed by a classifier 120 that determines whether the patient is experiencing a myocardial infarction 121. (This analysis is illustrative; one or more embodiments may perform any types of analyses on any types of waveform data from any types of devices.) The classifier 120 may for example use a neural network, or any other type of classification technology.

Figure 2:
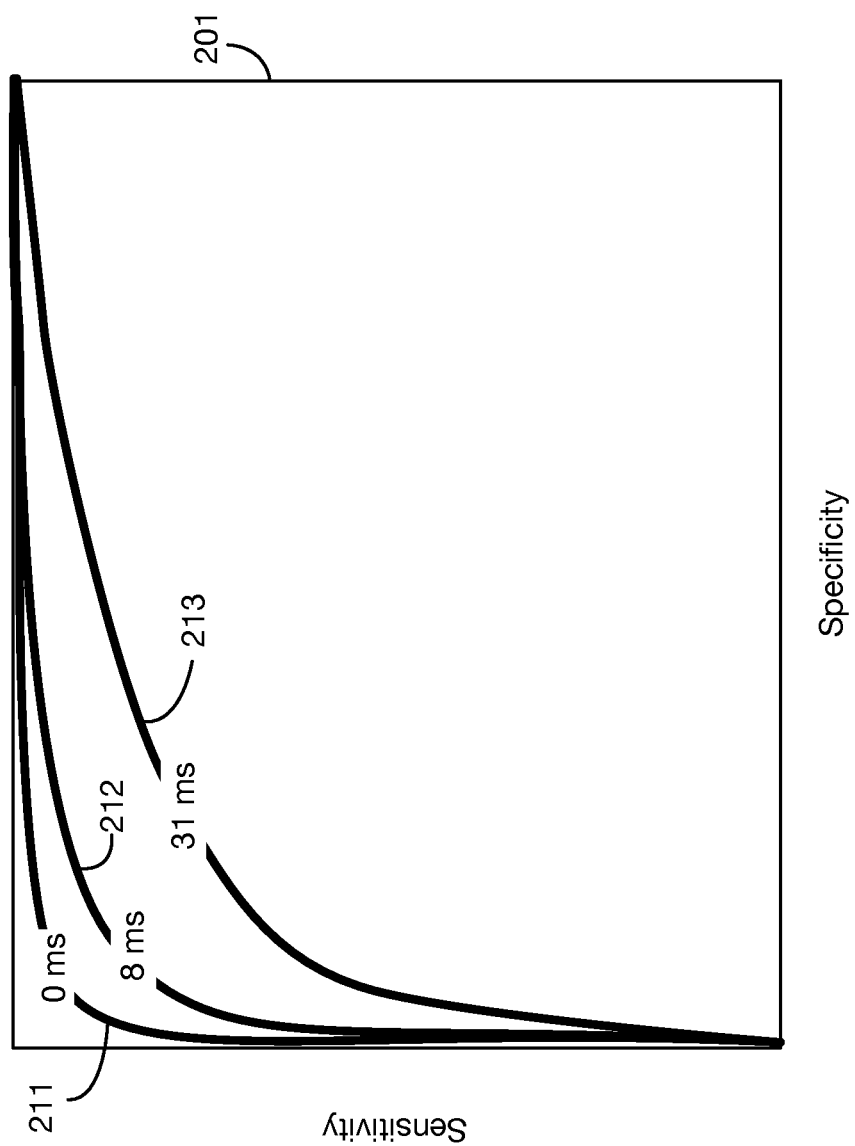
FIG. 2 continues the example of FIG. 1 to show that that time misalignment between the waveforms can dramatically reduce the classifier performance; accurate synchronization of waveforms to within a very small number of milliseconds is therefore critical.

A challenge for the analysis illustrated in FIG. 1 is that transmission of sample data from device 101 over network 103 may cause misalignment of some or all of the waveforms. Packets sent over network 103 may be subject to variable and unpredictable delays, which can cause waveforms to be out of synchronization. Small misalignments among waveforms of even several milliseconds can dramatically reduce the performance of classifier 120 or similar analysis algorithms. This situation is illustrated in FIG. 2, which shows the results of experiments performed by the inventors to test the effect of different amounts of waveform misalignment on performance of the myocardial infarction classifier 120. Plots 201 show receiver operating characteristic (ROC) curves for classifier 120 with three different amounts of waveform misalignment: curve 211 show the ROC curve for no misalignment; curve 212 shows the ROC curve for 8 milliseconds of misalignment; and curve 213 shows the ROC curve for 31 milliseconds of misalignment. These results illustrate that millisecond-level waveform alignment is critical for maximum performance of the analysis algorithm.

Figure 3:
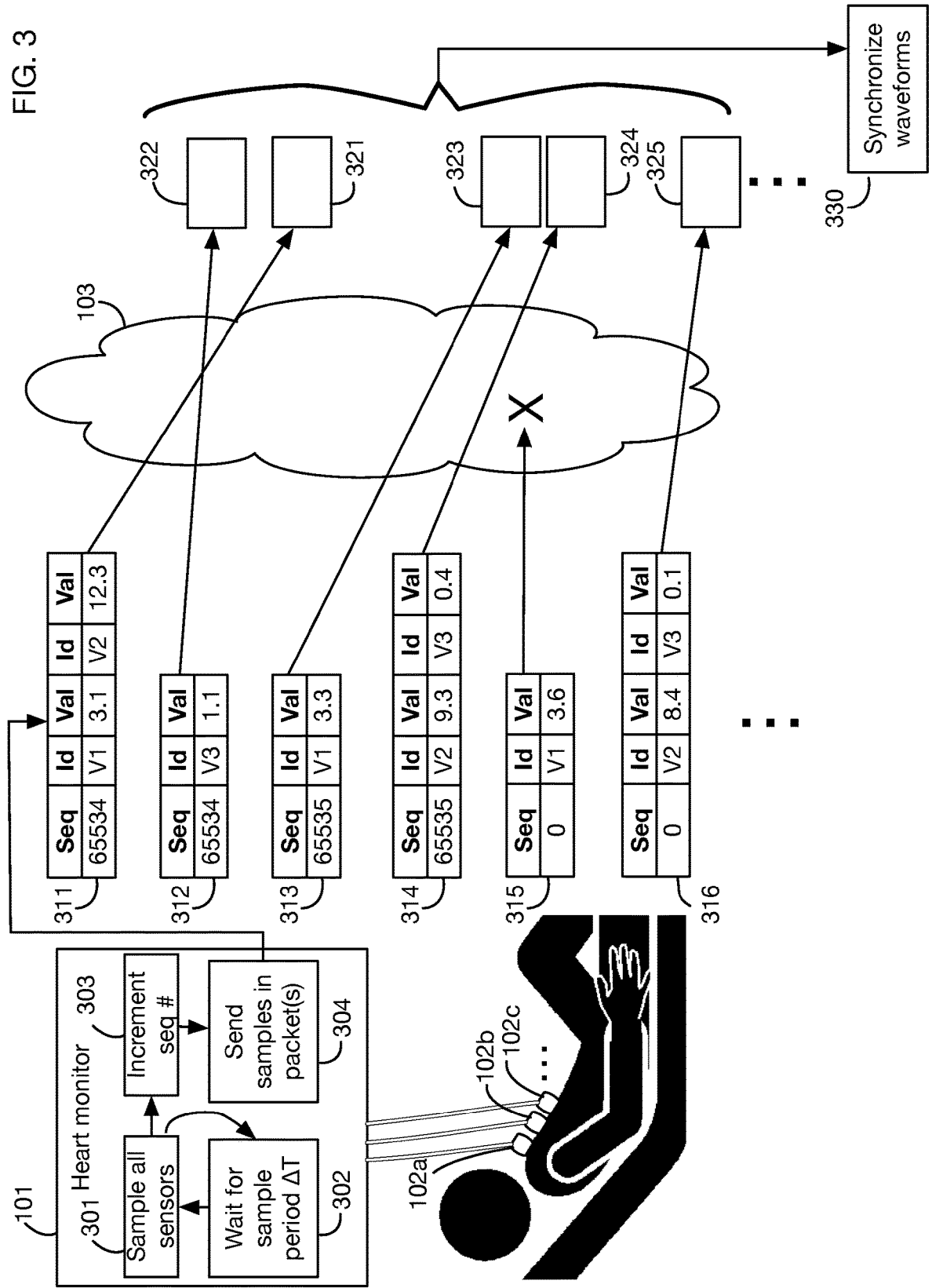
FIG. 3 shows transmission and receipt of illustrative packets containing waveform data; because the network transport carrying the datagrams may be connectionless, packets can be delayed, reordered, or lost.

FIG. 3 shows an example of data transmission from device 101 through network 103, illustrating the potential challenges in aligning waveforms after receiving the transmissions. Device 101 performs a sampling loop to sample all of its sensors at a regular sampling period, which may be for example 256 milliseconds for a heart monitor. Each sampling cycle has a duration of approximately the same sampling period. This sampling continues periodically over a time interval, which may be seconds, minutes, hours, or days. Sampling step 301 collects data from each sensor in the device (for example by polling each sensor and digitizing the sensor's analog value); sampling then waits in step 302 before sampling again after the sampling period has elapsed. This loop occurs repeatedly while the monitor is running. For each sample (of all sensors), the monitor performs an increment 303 of an internal sequence number, which is used to tag the transmitted samples (as described below). This sequence number may be a fixed number of bits (such as 16 bits, for example), and may rollover when the maximum sequence number value is reached. The sequence number may rollover to the minimum value. For example, with a bit length of k bits, treated as an unsigned integer, the minimum sequence number is 0, the maximum sequence number is $2^k-1$, and there are $2^k$ distinct sequence numbers. When the device increments the maximum sequence number $2^k-1$, the sequence number rolls over to 0. Sequence numbers therefore may not uniquely identify a sample. The samples collected in sampling step 301, and the sequence number generated by increment 303, are then transmitted over network (or networks) 103 in step 304. The collection of samples from all sensors (for a single sampling cycle) may not necessarily all be sent in the same packet.

FIG. 3 shows illustrative packets 311 through 316 that may be sent successively from device 101 over network 103. For ease of exposition, these illustrative packets show only data from 3 sensors 102a, 102b, and 102c; in practice any number of sensors may be associated with a device. Each sensor is assigned an identifier; thus sensor 102a may correspond to heart monitor lead "V1", sensor 102b may correspond to heart monitor lead "V2", and sensor 102c may correspond to heart monitor lead "V3". During the initial sampling cycle, sequence number 65534 is assigned, and values 3.1, 12.3, and 1.1 are read from sensors 102a, 102b, and 102c, respectively. The first packet 311 transmitted contains the sequence number and the values for sensors 102a and 102b; the second packet 312 contains the sequence number and the values for sensor 102c. In the next sampling cycle, the sequence number is incremented to 65535, and values 3.3, 9.3, and 0.4 are read. Packet 313 is sent with the sequence number and the value from sensor 102a, and then packet 314 is sent with the sequence number and the value from sensors 102b and 102c. In the third sampling cycle, values 3.6, 8.4, and 0.1 are read, and the sequence number is incremented but it rolls over to 0 (with a 16 bit sequence number). Packet 315 is sent with the sequence number and the value from sensor 102a, and then packet 316 is sent with the sequence number and the values from sensors 102b and 102c.

Network 103 may provide any type or types of transmission of packets 311 through 316 to a receiving system or systems. In one or more embodiments, transmission may be unreliable and subject to issues such as packet loss, packet reordering, and variable and unpredictable packet delays before delivery. These issues may occur for example when a connectionless transport layer such as UDP (User Datagram Protocol) is used to send packets. FIG. 3 illustrates some of the situations that may occur with packet transmission. Packet 311 is sent before packet 312, but packet 312 arrives first. Packet 313 arrives after a long delay, and then packet 314 arrives very shortly thereafter. Packet 315 is lost.

The received packets 322, 321, 323, 324, and 325 are then processed by one or more receiving systems. Some of this processing may require a synchronization process 330 of the waveforms. This synchronization 330 may be performed by one or more synchronizing processors that may receive packets over one or more network connections. This synchronization cannot simply use the received time of packets directly because of the variable packet delays, reorderings, and losses described above. A system and method to synchronize waveforms that accounts for these transmission issues is described below.

Figure 4:
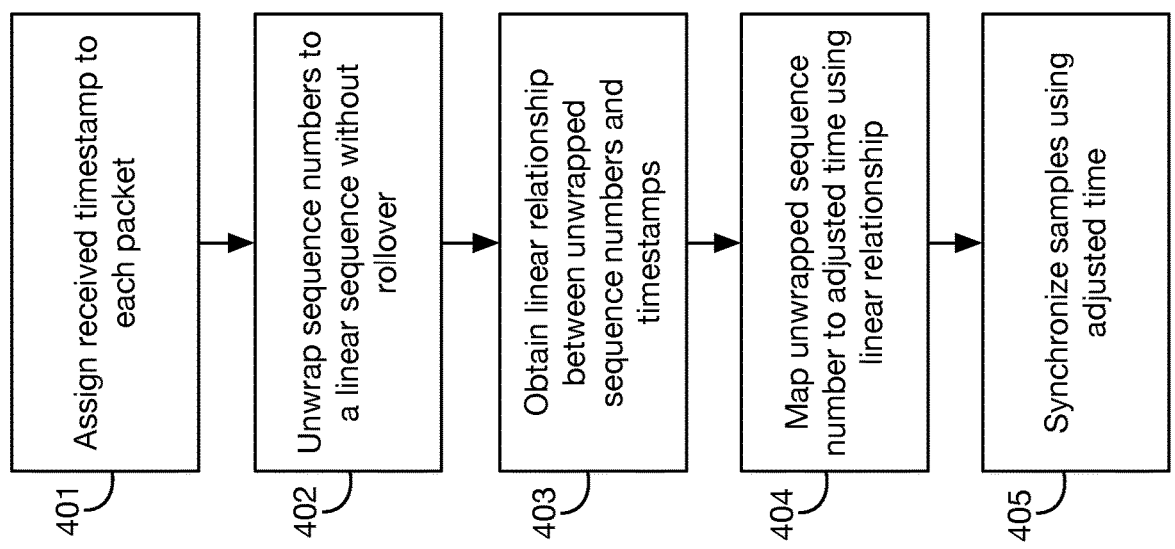
FIG. 4 shows an illustrative flowchart of steps that may be used in one or more embodiments of the invention to synchronize waveforms.

FIG. 4 shows a flowchart of illustrative steps that may be used in one or more embodiments to generate synchronized waveforms from the packets received from a device. In step 401, a receiving system assigns a received timestamp to each packet. In step 402, the sequence numbers in the packets are "unwrapped" to undo the effects of rollover: the unwrapped sequence numbers will form a linear sequence with no rollovers. In step 403, a linear relationship is obtained between the unwrapped sequence numbers and the received timestamps assigned in step 401. In step 404, this linear relationship is used to map the unwrapped sequence numbers to an adjusted time. Finally in step 405, the waveforms are synchronized using the adjusted times. These steps are described in greater detail below.

Figure 5:
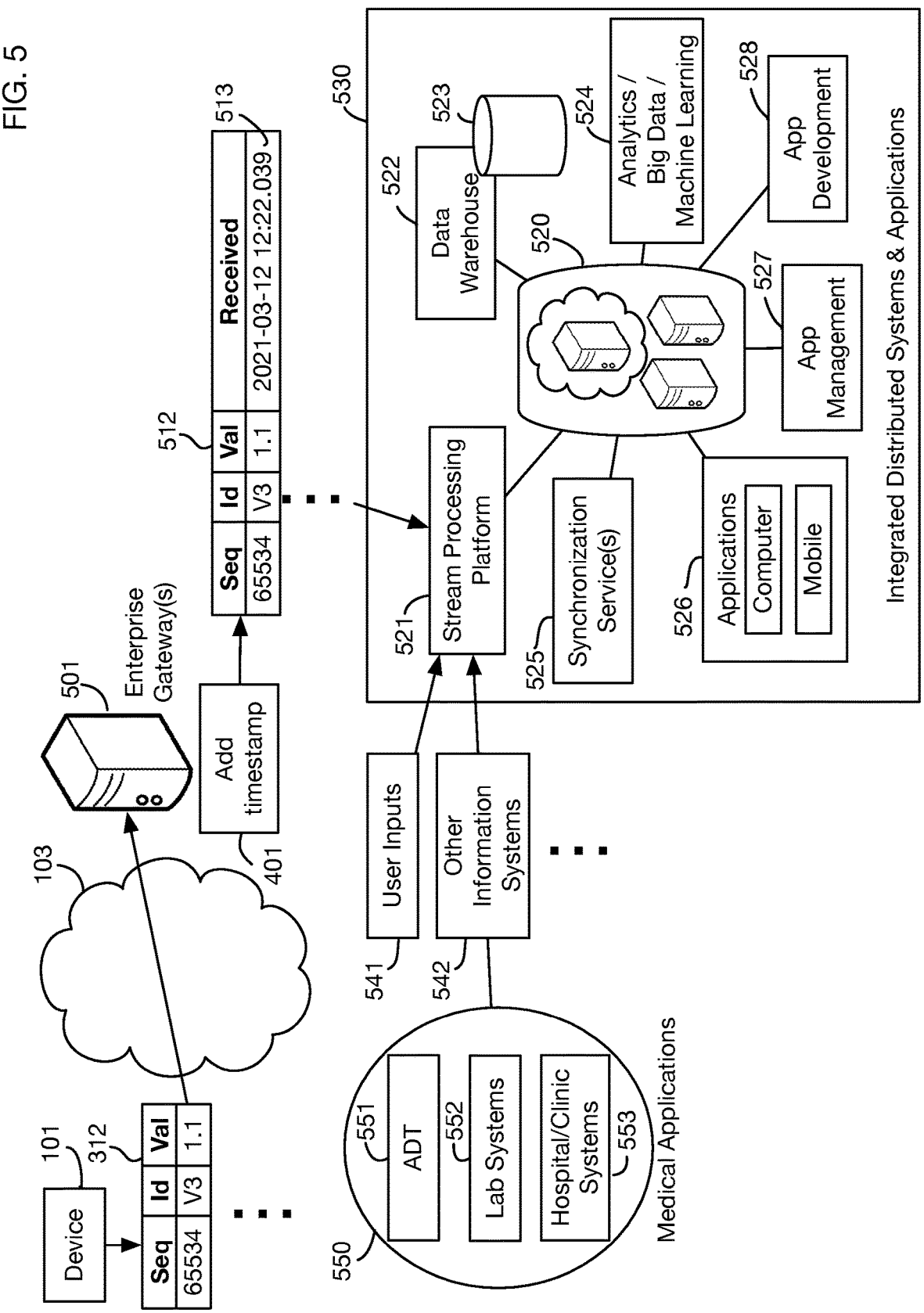
FIG. 5 shows an illustrative architecture of software and hardware components that may be used in one or more embodiments of the invention to receive, store, and process waveform data and other information.

FIG. 5 shows an illustrative architecture of hardware and software components that may receive, store, or process waveform data or other information, and that may incorporate some or all of the synchronization steps described in FIG. 4. Packets such as packet 312 sent from device 101 over network or networks 103 may be received by one or more receiving processors 501, which may be for example an enterprise gateway or similar system. (Other systems or nodes may receive and forward packets before packets reach this system 501.) This system 501 performs timestamping step 401 to add a timestamp to each received packet corresponding to the system clock when the packet is received and processed. In one or more embodiments, multiple receiving processors 501 may receive and process packets. The clocks of the receiving system or systems may be synchronized for example using NTP (network time protocol).

Timestamping step 401 transforms packet 312 to augmented packet 512, which contains the same data as packet 312 as well as the timestamp 513 of when the packet was received by system(s) 501. The stream of augmented (timestamped) packets such as 512 may then be transmitted to system 530, which may for example be an integrated, interconnected, and potentially distributed collection of processors, applications, and storage subsystems. Timestamped packets such as packet 512 may be streamed to a stream processing platform 521, or a distributed set of stream processing platforms, which may transform or forward streams to other system components. In one or more embodiments, other data in addition to waveform data may also be streamed or otherwise transferred to system 530, such as data from other information systems 542 and user inputs 541. For example, in a medical application, information systems 550 that may be connected to system 530 may include systems such as ADT (admission, discharge, and transfer) systems 551, laboratory systems 552, and hospital or clinic information systems 553.

The applications and data storage subsystems integrated into system 530 may be executed or managed by one or more processors 520, which may include the receiving system(s) 501 as well as any other servers or other computers. Any of these systems may be or may have any type or types of processors, including for example, without limitation, desktop computers, laptop computers, notebook computers, CPUs, GPUs, tablet computers, smart phones, servers, customized digital or analog circuits, or networks of any of these processors. Some or all of these systems may be remote from the site housing device 101. Some or all of the systems may be cloud-based resources, such as for example AWS® servers or databases. Data and processing may be distributed among the processors 520 in any desired manner. Illustrative embodiments of system 530 may include any number of stream processing components such as AWS Kinesis® or Apache KAFKA® with KSQL® or SPARK®, database components, computational components, data warehouse, data lake or data hub components, analytics components, and applications components. Applications may be managed by an application management subsystem 527, which may for example manage deployment, distribution of processing across processors, and data interconnections among components. An application development platform 528 may also be connected to the other components of system 530, so that new or modified applications can access streams, data, and component outputs for development and testing.

The stream processing platform 521 (which may be a distributed network of stream processing systems) may provide immediate access to received packets by applications that are part of or connected to system 530. For example, in a medical embodiment these applications may include algorithms for detecting and predicting cardiac arrhythmia, physiological decompensation and diverse types, cardiac and respiratory events, inadequate blood pressure and/or blood oxygen and glycemic instability. System 530 may utilize waveform data to inform clinicians, extract features indicative of patient physiological state (such as heart rate variability), support predictive applications, enable application development, and display results at local and remote locations.

As described for example with respect to FIGS. 1 and 2, accurate results may necessitate waveform alignment which may be performed by synchronization service(s) 525 as packets are received by the stream processing engine 521.

Data received by stream processing platform 521, or from other sources or subsystems, may be stored in one or more databases or other storage systems 523, which may implement or connect to data warehouses, data lakes, or data hubs 522. System 530 may provide access to data stored in any database, data warehouse, data lake, or data hub, to applications 526, which may include computer-based applications and mobile apps. Stored data or directly streamed data may also be processed by analytical systems 524, which may for example include machine learning and big data analytics. In medical applications, data may be processed in bulk to provide representative data sets for determining models capable of detecting and predicting clinical conditions and events and patient state, such as the myocardial infarction classifier 120 described with respect to FIG. 1. Analytics 524 and applications 526 may require synchronization of waveform data; synchronization services 525 may perform this synchronization before storage, upon retrieval from storage, or on streamed data as it is received. A user or subsystem may for example request synchronization of waveforms for a specific patient or for multiple patients over a particular time interval or intervals.

System 530 may also provide application access to data stored in the database, data warehouse, data lake and/or data hub for user consumption for offline viewing, reporting, annotation and chart review. Here, synchronization 525 may be applied to waveform either prior to insertion into the database or data warehouse or after querying for the desired data subset.

In summary, synchronization services 525 may be applied to incoming streams received by stream processing platform 521, or to data stored in subsystems 523 and 522, either before or after storage. Appropriate synchronization of waveform data may be critical to accurate analysis and display by analytics 524 and applications 526.

Figure 6:
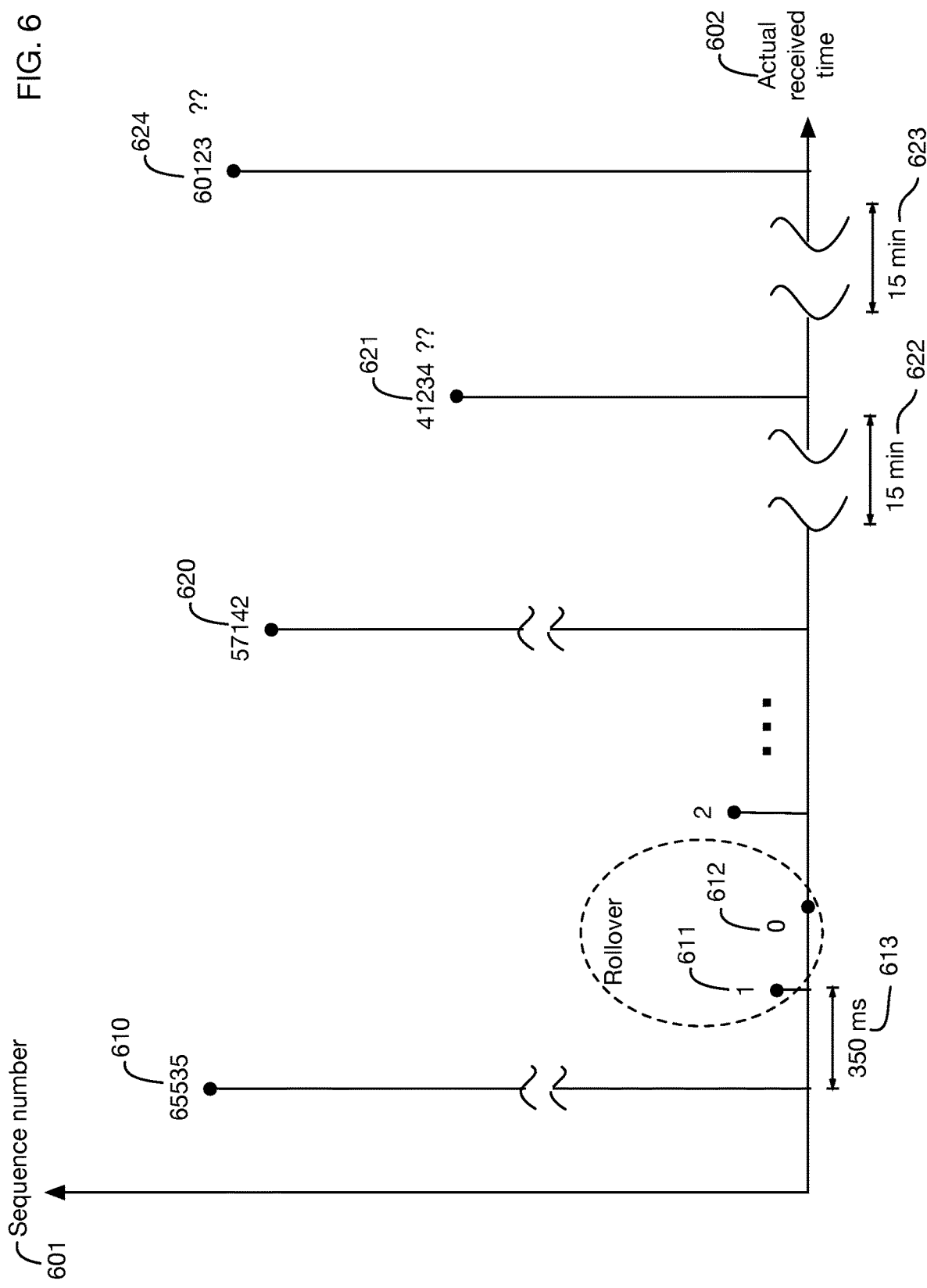
FIG. 6 illustrates the issue of rollover of sequence numbers in transmitted packets, and the particular challenge of unwrapping sequence numbers after long delays between packets.
Figure 7:
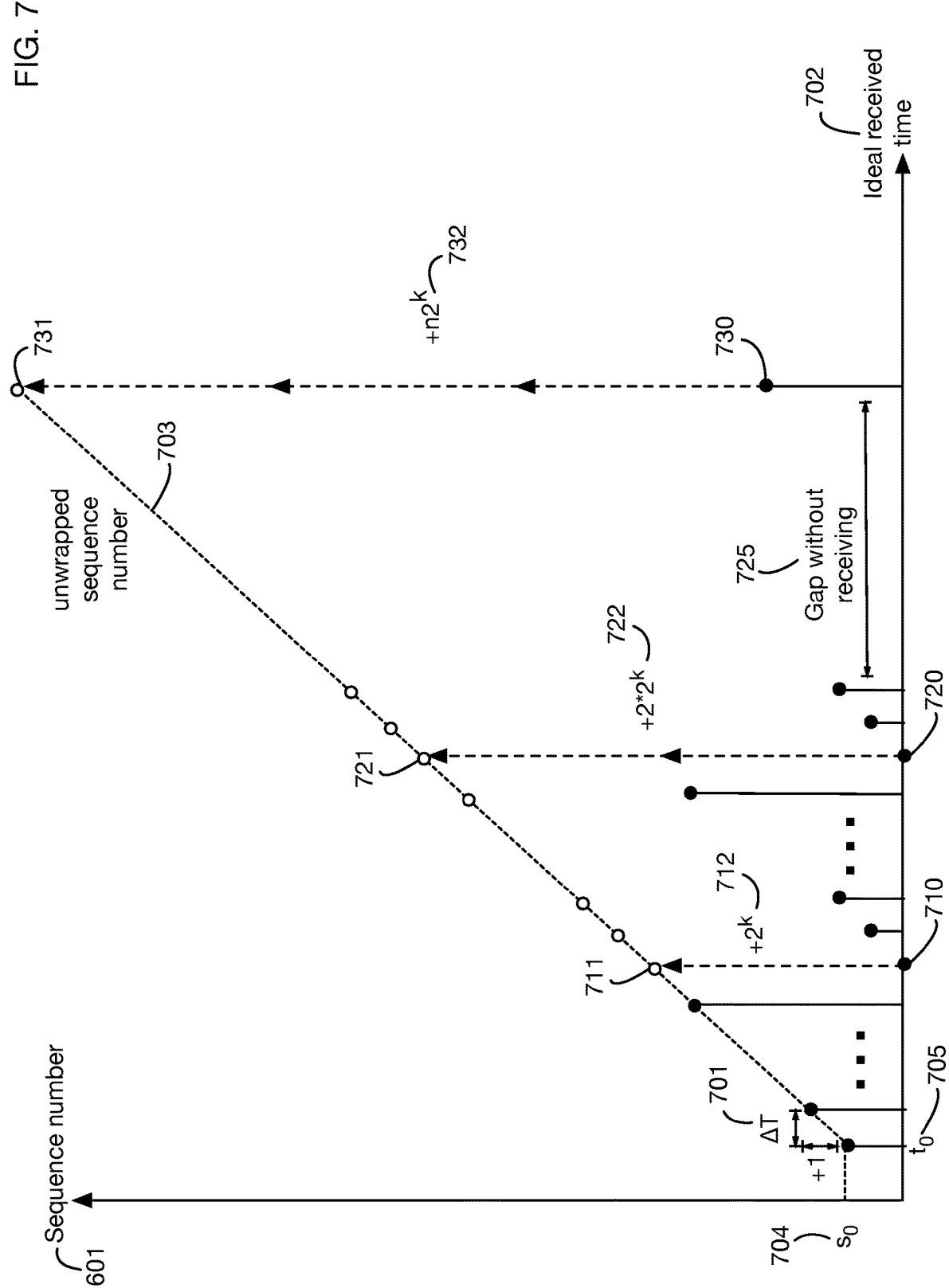
FIG. 7 illustrates how unwrapped sequence numbers are correlated with the received time of packets.
Figure 8:
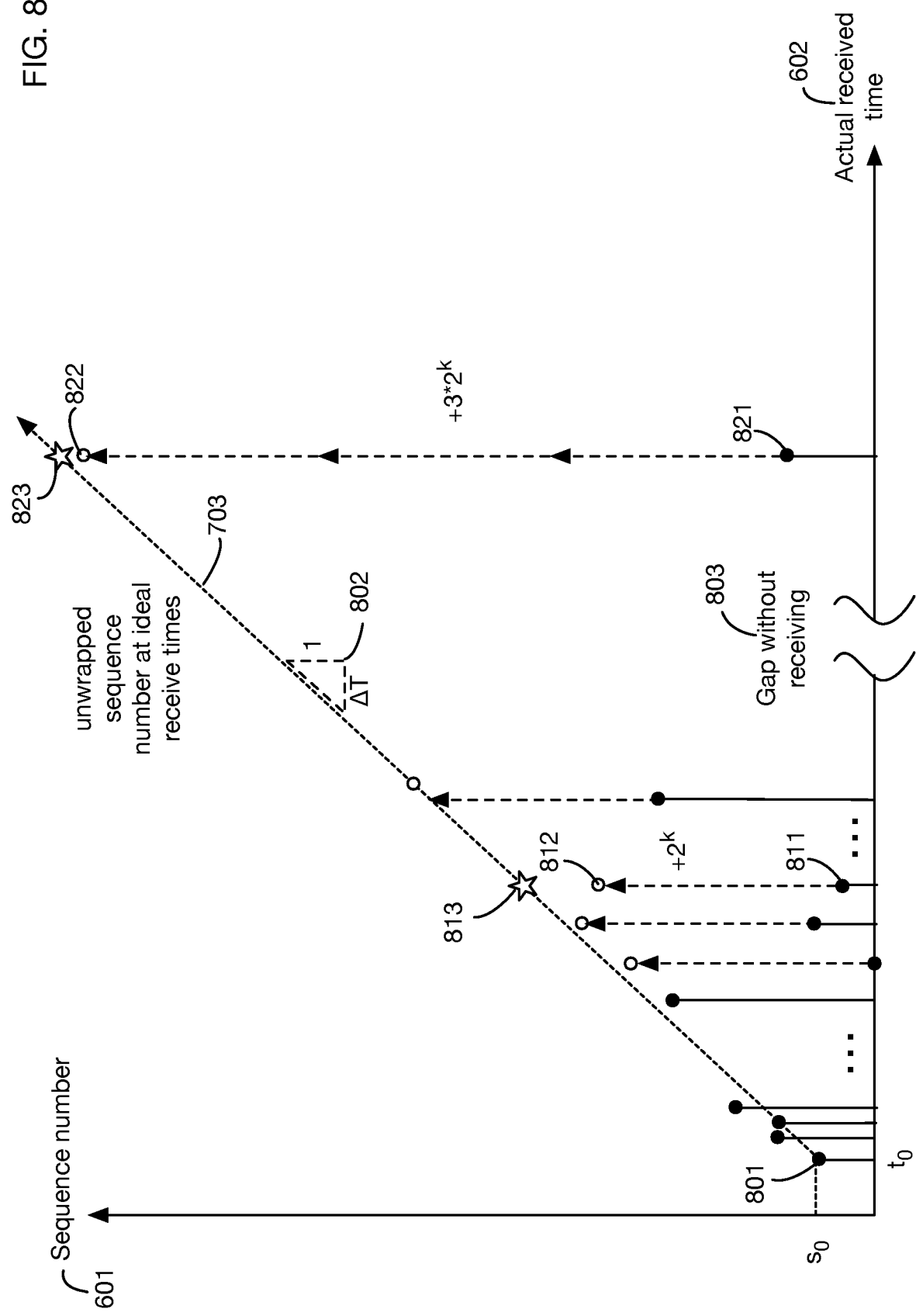
FIG. 8 illustrates a method that may be used to unwrap sequence numbers that adds an integral multiple of the sequence number period to each wrapped sequence number to get close to a linear curve based on the received time.

We now describe an illustrative procedure that may be used in one or more embodiments to perform synchronization 525 on waveform data that has been received and timestamped. FIGS. 6, 7, and 8 illustrate an approach to step 402, unwrapping of sequence numbers. The objective of this step is to assign a unique unwrapped sequence number to every sampling cycle in the device, and to undo the effect of potential wraparound of sequence numbers due to the finite and fixed bit length of a sequence number field. The unwrapped sequence numbers may then be used for synchronization, as described below.

If packets were always received reliably and in order, with no gaps, unwrapping sequence numbers would be straightforward. For example, with a 16-bit sequence number (treated as an unsigned integer), the maximum sequence number would be 65535, and the following sequence number would be 0 (the minimum sequence number value). This would indicate that a wraparound has occurred, and the unwrapped sequence number could simply be set to 65536. After a single wraparound, the unwrapped sequence number is the sum of the wrapped sequence number and the sequence number "period", which is equal to the number of distinct wrapped sequence numbers. This sequence number period is $2^k$ for a sequence number of k bits. However, because packet delivery can be unreliable, with reordering, loss, and unpredictably long delays, unwrapping of sequence number is more complex. FIG. 6 illustrates the potential challenge. The chart shows the sequence number 601 of received packets as a function of the received timestamp 602. A 16 bit sequence number is used for illustration; similar issues and techniques may apply to sequence numbers of any length. This example also assumes that the sampling period for the transmitting device is 256 milliseconds. The first packet received 610 has sequence number 65535, which is the maximum value for a 16 bit unsigned integer. After a delay 613, a second packet 611 is received with sequence number 1. Because the delay 613 is of the same order of magnitude as the device's sampling period, it is almost certain that a rollover has occurred in the sequence numbers. Sequence number 1 can therefore be mapped to unwrapped sequence number 65537. Similarly the next packet received 612 has sequence number 0, which almost certainly indicates the rollover happened after packet 610. In this case, packets 611 and 612 were reordered in transport, but it is straightforward to detect and compensate for the rollover, by mapping 1 to 65537, and 0 to 65536. A more complex scenario occurs after packet 620, when a long delay 622 passes before the next packet 621 is received. In this situation it is not apparent whether packet 621 indicates a rollover, a late packet without rollover, or possibly multiple rollovers. In another scenario, another long delay 623 passes between receipt of packet 621 and the next packet 624. In this scenario, the sequence number of packet 624 is greater than that of packet 621, but it is not clear from the sequence numbers alone whether a rollover may have occurred between these two packets.

FIGS. 7 and 8 show a procedure that may be used to determine the unwrapped sequence number for any packet, even with issues such as those described above. FIG. 7 shows a simplified scenario, and FIG. 8 describes the complete solution. In the (artificial) example shown in FIG. 7, perfect network transmission is assumed where all packets are delivered in order with a fixed delay. This example also shows only a single packet per sequence number. In this simplified scenario, a new packet arrives after every time interval 701 that is equal to the device polling period (such as 256 milliseconds). The unwrapped sequence number can therefore be predicted perfectly from the (ideal) received time 702 of the packet. A line 703 mapping the received time 702 into the unwrapped sequence number can be generated by starting at the first point at received time 705 and received sequence number 704, where the line has slope $1/\Delta T$, where $\Delta T$ is the sampling period 701 of the device. Using this line, packet received times can be used to unambiguously determine the unwrapped sequence number. For example, received packet 710, with sequence number 0, can be mapped to unwrapped sequence number 711; the unwrapped sequence number is exactly a power of two 712 (corresponding to the sequence number period $2^k$ for a sequence number of k bits). At the next rollover, received packet 720 can be mapped to unwrapped sequence number 721, which is an offset 722 of a multiple of the sequence number period. Even if a gap 725 occurs, a subsequent received packet 730 can be mapped to unwrapped sequence number 731 based on the received timestamp.

FIG. 8 presents a more realistic example, wherein packets can be reordered, lost, or delayed by arbitrary amounts. The same procedure described with respect to FIG. 7 can be used to generate line 703 through the initial point 801 with slope 802, which maps received time 602 of each packet into an unwrapped sequence number. This mapping may not be exact, since packet receive times are not completely regular. However, it can be used to obtain a predicated approximate unwrapped sequence number, which can then be adjusted. For example, point 811 can be mapped to predicted approximate unwrapped sequence number 813 on line 703 using the packet's received timestamp. This unwrapped sequence number 813 cannot be exactly correct, because it does not differ from the wrapped sequence number by a multiple of the sequence number period. The point 812 differs from point 811 by the sequence number period ($2^k$), and it is relatively close to line 703; therefore this point 812 is the correct unwrapped sequence number.

Similarly even after a long gap 803 without packets, a packet 821 can be mapped to a predicated approximate unwrapped sequence number 823 based on the received timestamp of the packet. This value can then be adjusted to value 822, which differs from the wrapped sequence number an integral multiple of sequence number period. This procedure can be applied in general: the unwrapped sequence number can be determined as the value differing from the wrapped sequence number by an integral multiple of the sequence number period that is closest to the line 703.

The next step 404 remaps the unwrapped sequence numbers to adjusted times, which may then be used in step 405 to synchronize waveforms. This mapping is generally a linear mapping so that it reflects the periodic sampling that occurred in the device before transmitting packets. A linear mapping from unwrapped sequence numbers to adjusted times may be determined using various methods. A first illustrative approach that may be used is to calculate a line through the unwrapped sequence number and received timestamp of the packet with the lowest received timestamp, and through the unwrapped sequence number and received timestamp of the packet with the highest received timestamp. This line effectively uses the average received rate of packets as the adjusted time interval between successive unwrapped sequence numbers. A second illustrative approach is to calculate a line through the unwrapped sequence number and received timestamp of the packet with the lowest received timestamp, with the line slope equal to the sampling period of the device (such as 256 milliseconds). A third illustrative approach is shown in FIG. 9A. This figure shows received packets' received timestamps 602 as a function of their unwrapped sequence numbers 901. A linear regression line 902 may be fit to these points, and this line may be used to map each point to the adjusted time that lies on the regression line. For example, packet 911 may be mapped to adjusted received time 912 that is on regression line 902.

FIG. 9B illustrates the final synchronization step 405 that synchronizes data based on the adjusted time calculated for each packet. Top plot 931 shows waveforms 921a and 921b from two illustrative sensors of a device, using the received time 602 as the time axis. The waveforms are distorted due to variable packet delays and other time inaccuracies. Synchronization 405 remaps the time axis of each waveform to the adjusted time 902. Plot 932 shows the result of this step, with synchronized waveforms 922a and 922b.

Figure 10:
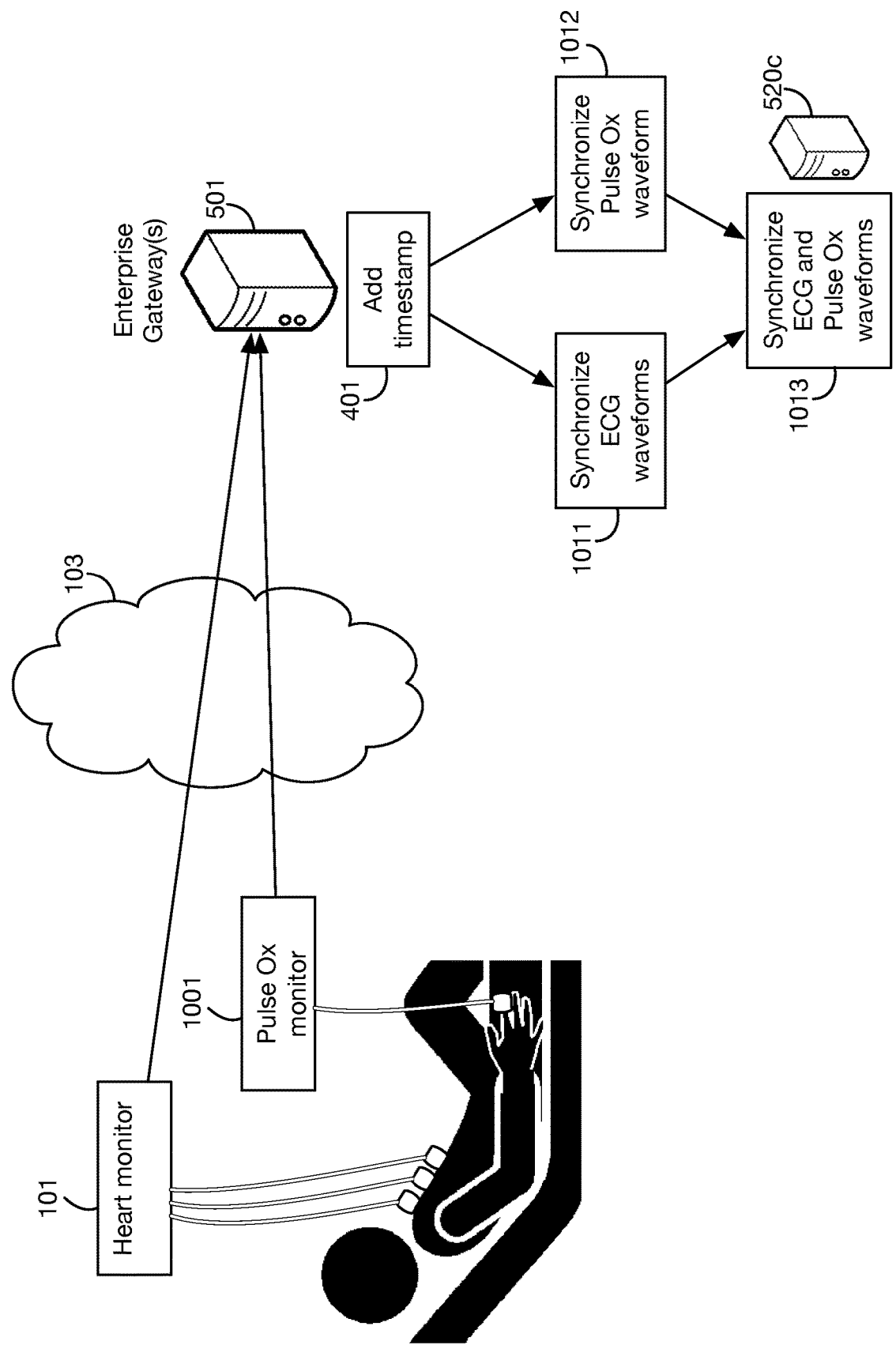
FIG. 10 illustrates an additional challenge of synchronizing waveforms across devices that may be addressed by one or more embodiments of the invention.

In some situations it may also be desirable to synchronize waveforms across multiple devices. This synchronization may be performed using an extension of the methodology described above. FIG. 10 shows an illustrative situation with two devices 101 and 1001 that monitor the same patient. Each device transmits packets over network or networks 103, and the packets are received by one or more servers 501 that perform step 401 to add received timestamps, as described above. On request or as needed, waveforms within each device are synchronized in steps 1011 and 1012, as described above. In some situations a final step 1013 may then be performed to synchronize waveforms across the devices, which is described below. This inter-device waveform synchronization may be performed by one or more inter-device synchronizing processors 520c. The processor or processors 520c that perform inter-device synchronization may be the same as or different from any of the other processors described above, such as enterprise gateway(s) 501 or servers 520.

FIG. 11 shows one illustrative approach to inter-device synchronization 1013. This approach is most effective when transmission latencies from the devices to the receiving server(s) 501 are roughly equal on average (even if individual packet delays may vary widely), and when a single receiving server is used or multiple receiving servers have closely synchronized clocks. The actual received time of packets then provides a common reference that can be used for synchronization. After mapping each packet to an adjusted time for each device, the adjusted times of the packets of interest can be modified by a constant amount for each device so that the average adjusted time equals the average received time; the waveforms between devices will then by time-synchronized. For example, plot 1100a shows the adjusted times 902a of packets from device 101 compared to their actual received times 602a, and plot 1100b shows the adjusted times 902b of packets from device 1001 compared to their actual received times 602b. The adjusted time bias 1102a for device 101 can be calculated for example as the average difference between the adjusted time and the received time for each packet, and similarly the adjusted time bias 1102b can be calculated for device 1001. The biases can be subtracted from each packet's adjusted time to synchronize the packets across devices. This procedure effectively centers packets' adjusted times on the line 1101 where adjusted times and received times are equal (on average).

Figure 12:
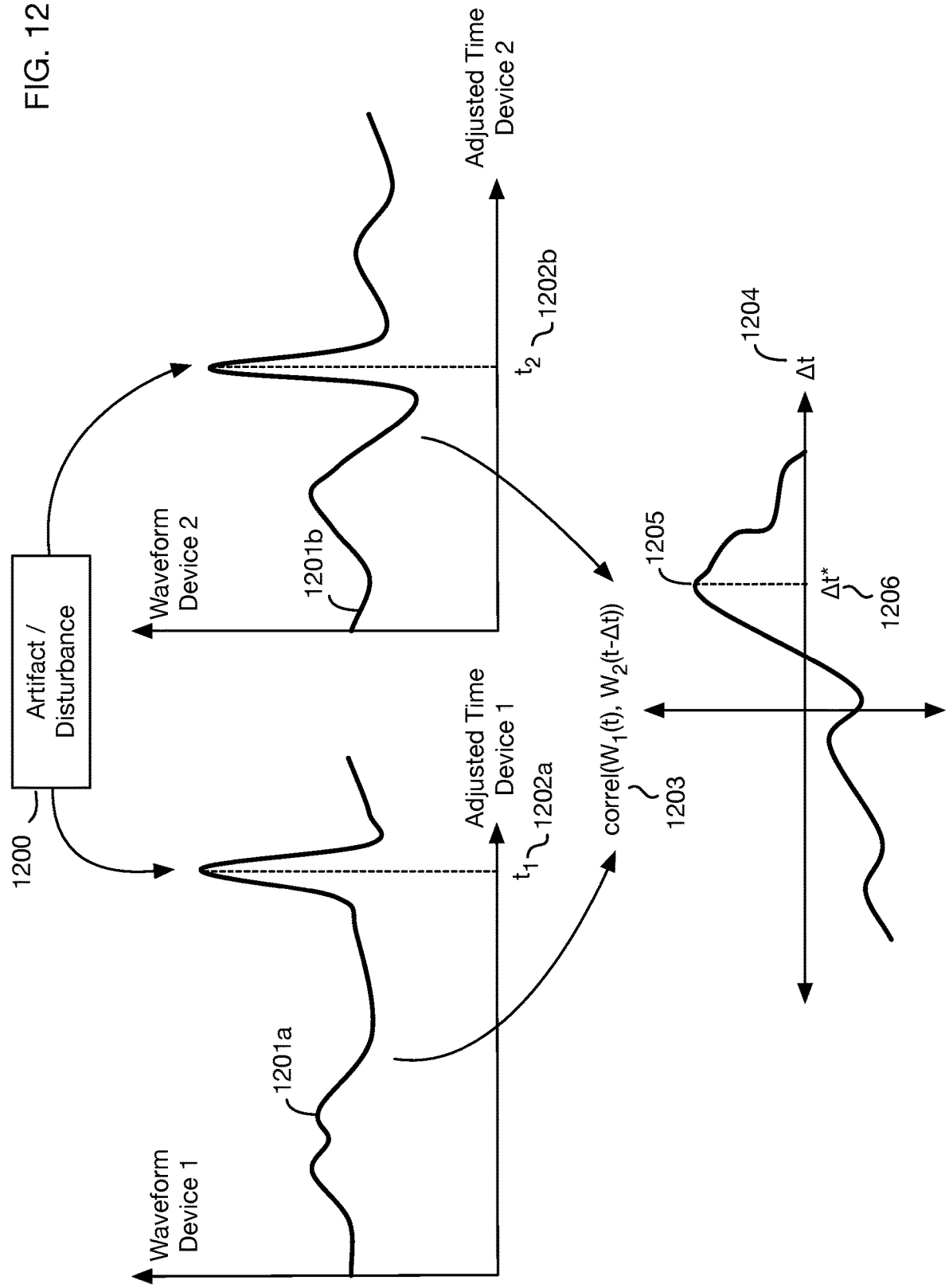
FIG. 12 illustrates another method that may be used to synchronize waveforms across devices, which uses an artifact that affects signals from multiple devices.

FIG. 12 illustrates another approach that may be used to synchronize waveforms across devices. In this approach, motion artifacts or other common disturbances that affect both devices may be used to determine the systematic time offsets between sensors connected to different devices that are connected to the same patient. For example, two pulse oximeters may be connected to the same individual but communicate through different devices each having a different set of sequence numbers. In the case of an ECG sensor, in addition to motion artifacts pacemaker signals may be used.

In this case, after synchronizing the waveforms associated with each device, measurement regions containing artifacts or common disturbances may be detected based upon a significant increase in spectral entropy and the lack of an associated periodic signal.

In the example shown in FIG. 12, artifact or disturbance 1200 affects signal 1201*a* from one device and signal 1201*b* from a second device. The artifact's effect is visible at adjusted time 1202*a* for the first device, and at adjusted time 1202*b* for the second device. The difference between these adjusted times 1202*b* and 1202*a* can be subtracted from the adjusted times for signal 1201*b* to synchronize the two devices' waveforms.

If the precise time of the artifact is not apparent in the signals, a cross-correlation 1203 can be performed between signals 1201*a* and 1201*b* with different time adjustments to one of the signals. The signals may for example be re-sampled to a common higher sampling frequency (e.g., 10×). The phase difference may be determined as the time offset 1206 associated with the maximum point 1205 of the curve 1203 generated via a cross-correlation calculation between the first waveform and time shifted versions of the second. To ensure a precise time offset, the maximum point may be further estimated as the zero crossing of the derivative of a locally fitted quadratic function. After determining the time offset between the first and second devices, the adjusted time axis of the second device may be adjusted by subtracting the time offset 1206.

In a large facility, for example a hospital with hundreds of patients and thousands of devices, very large amounts of data may be generated as devices stream their sensor readings and as other patient data sources, such as laboratory measurements and prescriptions, are integrated. It may be necessary or advantageous to store much or all of this data for subsequent analysis and data mining. This storage process 522 is shown in FIG. 5. With extreme amounts of data, however, storage presents significant challenges. One particular challenge is efficient indexing of data. Generating keys that uniquely identify each record of a database is essential to data warehousing. In addition to the uniqueness characteristic, the key must be immutable and easily indexed.

Figure 13:
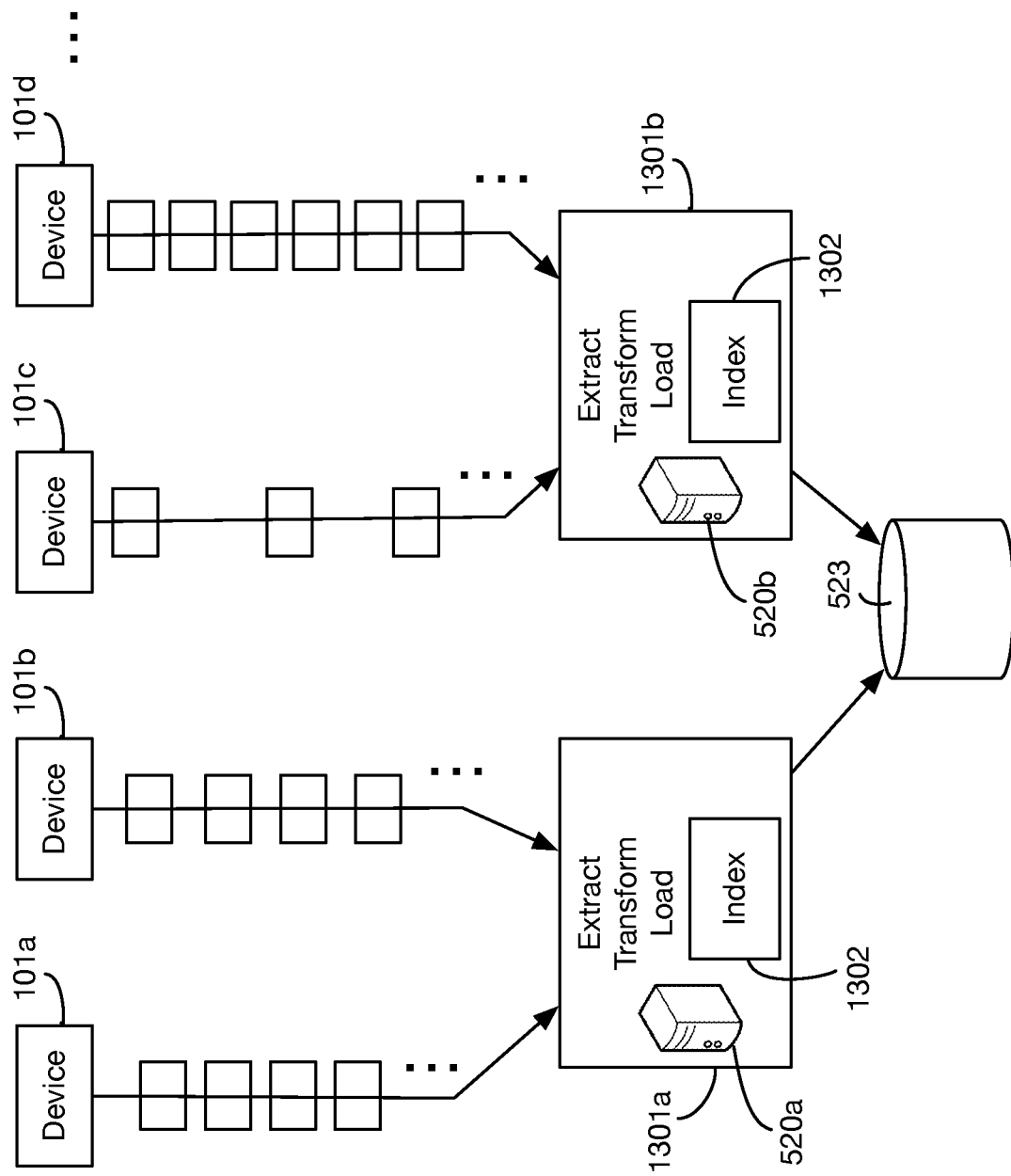
FIG. 13 illustrates an embodiment that indexes the data streamed from one or more devices, and stores the indexed data in a database or data warehouse.

A further challenge is that processing of the large number of data streams may require a distributed approach; a single server may for example not be able to process all streams simultaneously. This situation is illustrated in FIG. 13, where illustrative devices 101*a*, 101*b*, 101*c*, and 101*d* stream packets to two different subsystems 1301*a* and 1301*b*. Each of these subsystems performs ETL (extract, transform, load) on the streams, which includes indexing 1302 of the data with keys, and storage of the indexed data in one or more databases, data warehouses, or data lakes 523. Each subsystem may be associated with one or more data storage processors that perform any or all of these functions, such as processors 520*a* and 520*b*.

Because of the distributed ETL and the potentially large number of streams, generation of keys using a centralized solution (such as a single server that assigns unique keys via a sequence generator) may not be feasible. Centralized generators may also inhibit proper administration of decentralized systems which, for heightened security, limit access. Preferably keys should be generated using a deterministic mapping that can be applied independently by each subsystem 1301*a* and 1301*b* while ensuring key uniqueness. Although the generation of a GUID or other random key provides a potential solution, after insertion into a given table, other independent processes that reference the GUID's record would necessarily need to query the table to retrieve it, significantly reducing retrieval efficiency.

Figure 14:
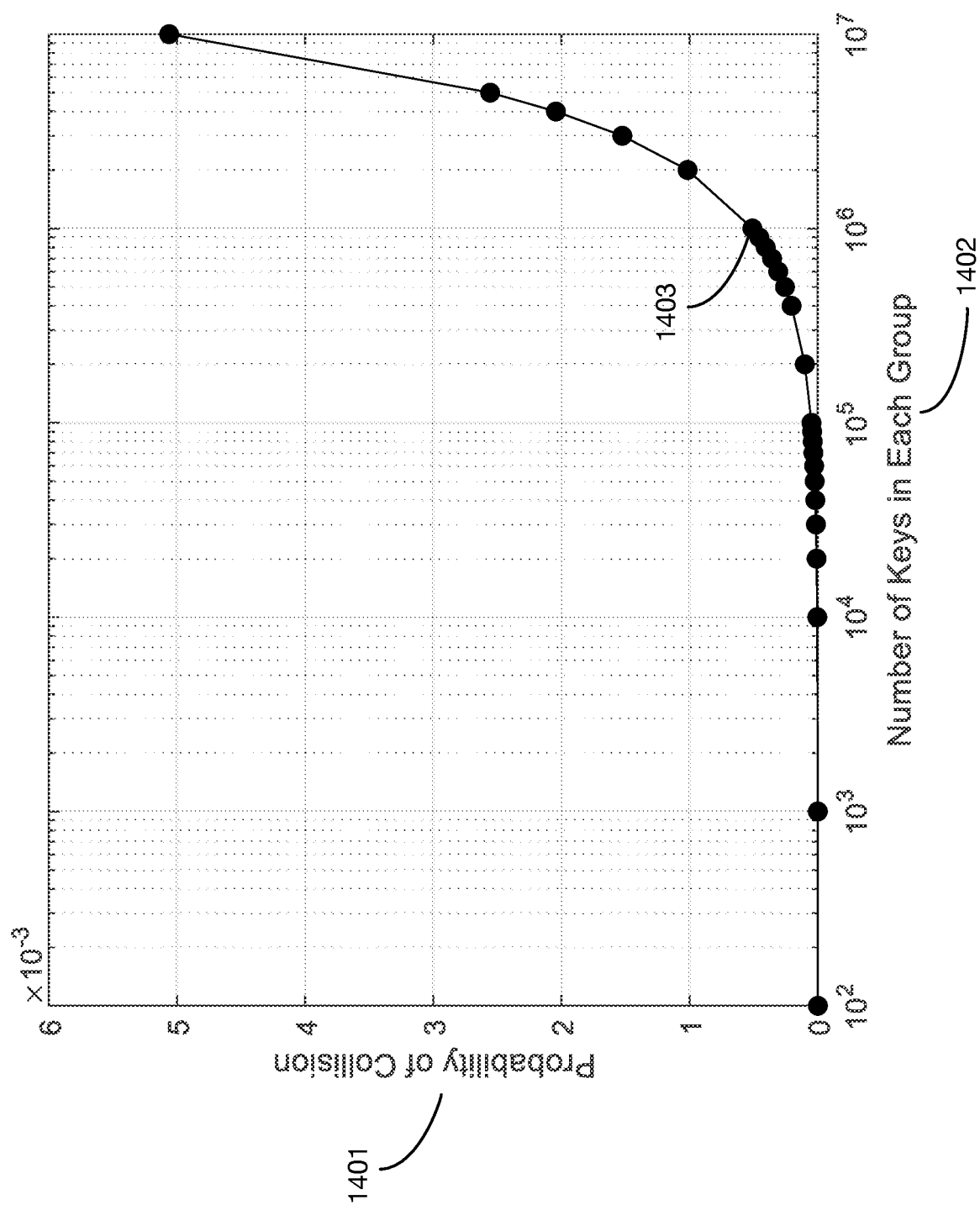
FIG. 14 shows a challenge with using hash codes as the index: the probability of hash collisions becomes large with millions, billions, or trillions of records.

A preferable distributed solution to key generation is a hashing algorithm, which deterministically maps some or all of the packet content into a hash code. Hashing also enables the calculation of a key without burdening the database via query. However, hashing algorithms are subject to hash collisions, which compromise uniqueness of keys or require post-processing to check for and address collisions. As the amount of data grows to millions, billions, or trillions of records a significant number of duplications will occur which will be destructive to the database. This issue is illustrated in FIG. 14, which shows experiments with hashing randomized 24 character alphanumeric strings to 9 digit hash codes. The chart shows the probability of each hash being a collision 1401 as a function of the number of hash codes generated 1402. Illustrative point 1403 shows that approximately 500 collisions will occur with 1 million generated hash codes.

The inventors have discovered a solution to the hash collision issue, which can be used in distributed systems and can accommodate the large amount of data generated by hundreds or thousands of streaming devices. This solution is to form keys as a combination of a prefix derived from the data and a hash code. Collisions between keys are thereby avoided as long as there are no hash collisions within a subset of data having the same prefix. This technique can greatly reduce the number of hash codes that must be unique.

An illustrative prefix that may be used in one or more embodiments is a time code that may be derived from the packet timestamp, for example. Illustrative time codes may be for example, without limitation, a year, a year and day-of-year, a year-day-hour, or a POSIX or similar date/time code or prefix or portion thereof. This code may be prefixed to a hash code of some or all of the content of a record, such as for example a hash code of a patient ID, a device ID, and a filename (derived from a date and time).

Figure 15:
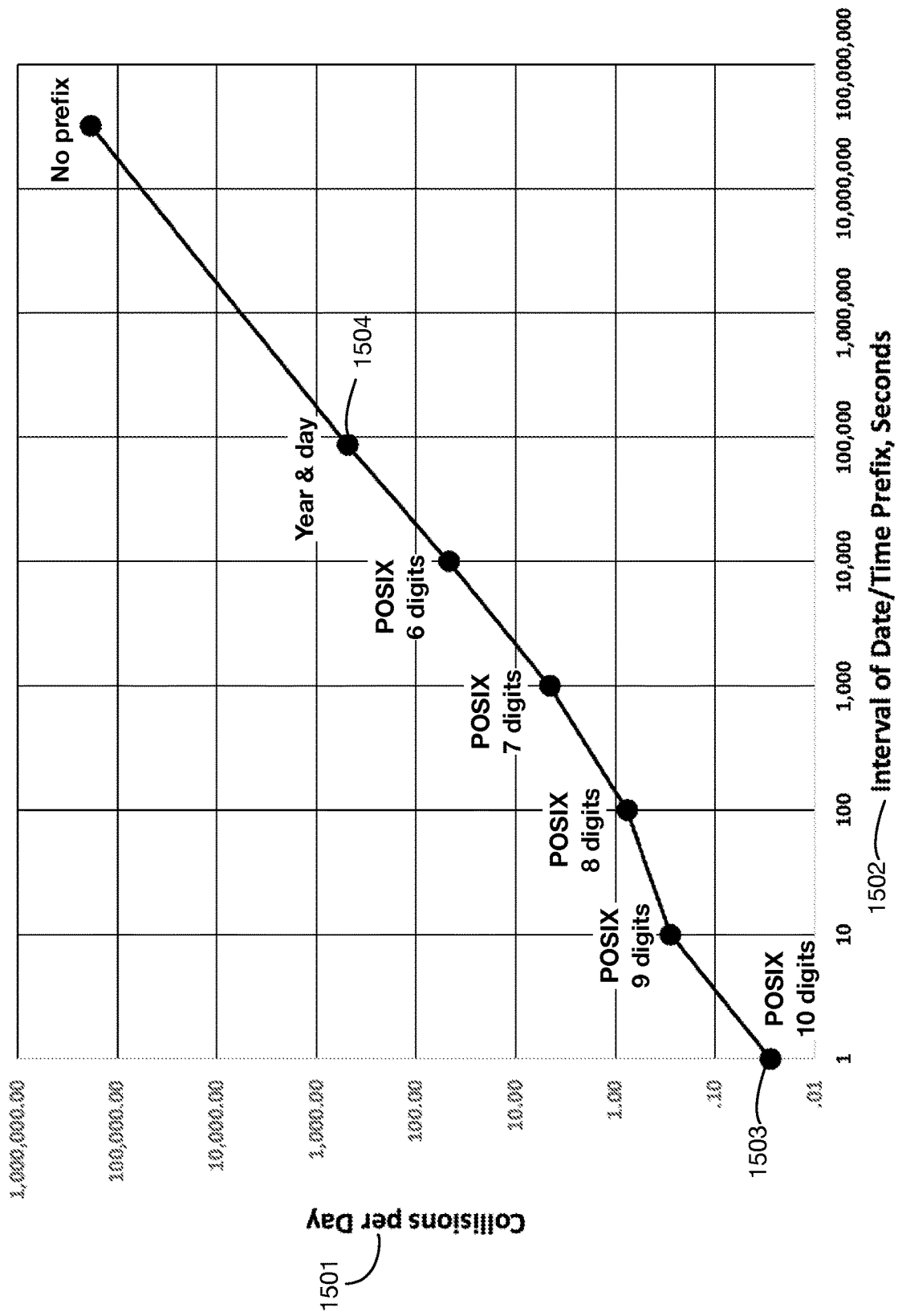
FIG. 15 illustrates a solution to the hash collision problem: prefixing the hash code with a date-time code, to reduce the number of indexes for which hashes should be unique.

FIG. 15 shows results of an experiment by the inventors for a simulated system that generates 1,000,000 records per day. The number of key collisions per day 1501 is shown as a function of the type of prefix used. Each prefix corresponds to a specific interval of time 1502 for which the prefix applies. For example, a 7-digit POSIX timestamp corresponds to an interval of 1,000 seconds. In this scenario, a prefix consisting only of the year and day-of-year 1504 still results in several hundred key collisions per day. A prefix consisting of a 10 digit POSIX timestamp 1503, which includes year, day, hour, minute, and second, results in a negligible number of collisions per day. The appropriate prefix may be selected based for example on the volume of data processed per day of the installation.

Figure 16:
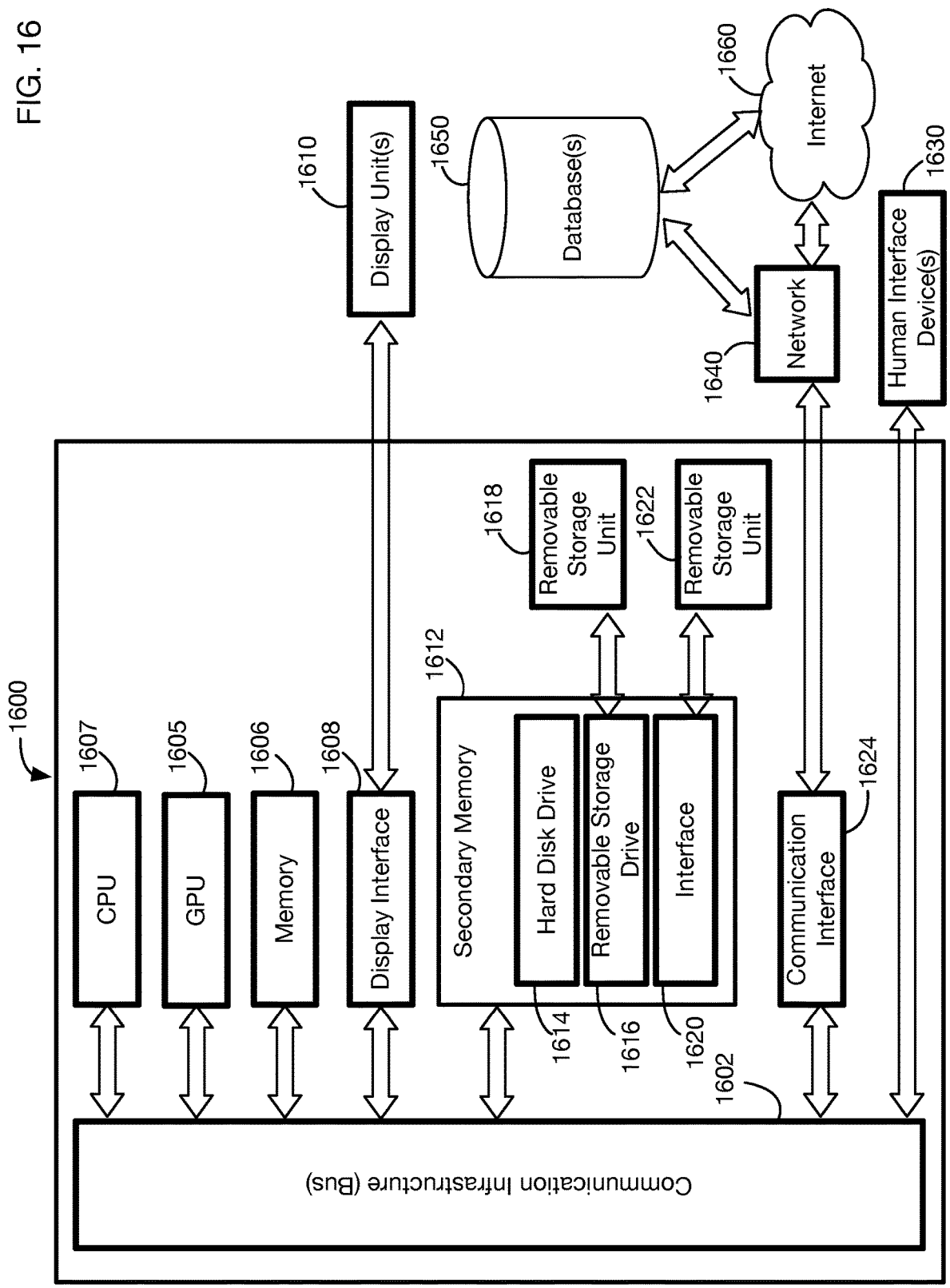
FIG. 16 shows illustrative computer hardware that may be used as or in any of the processors or systems described for the invention.

FIG. 16 shows an embodiment of exemplary computer 1600 that may be utilized in, by, or as any component in the system. In one or more embodiments, computer 1600 may be a network of computers, each of which may have any or all of the components shown in FIG. 16. In one or more embodiments, computer or computers 1600 may also be utilized to implement any function in the system, i.e., any step or act or function that executes in any computer or server or engine in the system. For example, computer or computers 1600 may be or may be a component of any transmitting device, such as device 101, any server or receiving or processing devices, such as servers 501 and 520. Computer or computers 1600 may for example execute or host any of the components of system 530, such as stream processing services 521, database 523, data warehouse 522, analytics 524, synchronization services 525, applications 526, application management 527, and application development 528. Computer or computers 1600 may for example be or be a component of any system 520c that performs cross-device synchronization 1013. It may be or be a components of any systems 520a and 520b that perform distributed indexing to generate keys for incoming data or events, which may then be distributed to any other system components. Computer 1600 may include processor CPU 1607 that executes software instructions specifically tailored to the respective functions of embodiments of the invention. The software instructions, otherwise known as computer program instructions, may reside within memory 1606. Computer 1600 may include processor GPU 1605, which may execute graphics instructions or other instructions for highly parallel operations, for example. GPU program instructions may also reside within memory 1606. Computer 1600 may include display interface 1608, which may drive display unit or units 1610 of any computer in the system as desired. Some computers 1600 may or may not utilize a display. Computer 1600 may include communication interface 1624, which may include wireless or wired communications hardware protocol chips. In one or more embodiments of the invention communication interface 1624 may include telephonic and/or data communications hardware. In one or more embodiments communication interface 1624 may include a Wi-Fi™ and/or BLUETOOTH™ wireless communications interface. Any wireless network protocol or type may be utilized in embodiments of the invention. CPU 1607, GPU 1605, memory 1606, display interface 1608, communication interface 1624, human interface devices 1630, secondary memory 1612, such as hard disk 1614, removable storage 1616, secondary memory interface 1620 and removable storage units 1618 and 1622 may communicate with one another over communication infrastructure 1602, which is commonly known as a "bus". Communications interface 1624 may communicate over any wired or wireless medium that allows for communication with other wired or wireless devices over network 1640. Network 1640 may communicate with Internet 1660 and/or database or databases 1650. Database 1650 may be utilized to implement any database, data warehouse, data lake, or data hub described herein.

While the invention herein disclosed has been described by means of specific embodiments and applications thereof, numerous modifications and variations could be made thereto by those skilled in the art without departing from the scope of the invention set forth in the claims.

What is claimed is:

1. A waveform synchronization system for data received from a network, comprising: one or more processors coupled to the network that is coupled to one or more devices, wherein each device of said one or more devices repeatedly samples data from one or more sensors over a time interval comprising multiple sampling cycles, each sampling cycle of said multiple sampling cycles comprising a duration of substantially a same sampling period;

said each device assigns a sequence number to each of said multiple sampling cycles, wherein said sequence number is in a range between a sequence number minimum value and a sequence number maximum value;

said sequence number assigned to a second sampling cycle of said multiple sampling cycles that is immediately after a first sampling cycle of said multiple sampling cycles equals said sequence number assigned to said first sampling cycle plus an increment;

when said each device increments said sequence number maximum value, said sequence number becomes said sequence number minimum value; and said each device comprises a sequence number period equal to a number of distinct sequence numbers between said sequence number minimum value and said sequence number maximum value;

said each device transmits over said network one or more packets corresponding to sampled data from said each sampling cycle, wherein each packet of said one or more packets comprises said sequence number corresponding to said each sampling cycle; and, said data from one or more of said one or more sensors that is sampled during said each sampling cycle;

one or more receiving processors of said one or more processors are configured to receive said one or more packets from said network and to add a received timestamp to said one or more packets to form a corresponding one or more augmented packets;

said network is configured to delay transmission of any of said one or more packets;

reorder any of said one or more packets; and, lose any of said one or more packets; and, one or more synchronizing processors of said one or more processors are configured to receive said one or more augmented packets corresponding to said multiple sampling cycles;

calculate an unwrapped sequence number for each of said one or more augmented packets corresponding to said multiple sampling cycles, wherein said unwrapped sequence number uniquely identifies each of said multiple sampling cycles;

calculate a linear relationship between said unwrapped sequence number and said received timestamp for said one or more augmented packets corresponding to said multiple sampling cycles;

apply said linear relationship to said unwrapped sequence number of said one or more augmented packets corresponding to said multiple sampling cycles to obtain an adjusted timestamp of each of said one or more augmented packets; and, synchronize said data across said one or more sensors over said time interval based on said adjusted timestamp to form synchronized data associated with said each device.

2. The waveform synchronization system of claim 1, wherein one or more of said one or more devices comprises a medical device.

3. The waveform synchronization system of claim 2, wherein
said medical device comprises a heart monitor; and,
each sensor of said one or more sensors is associated with a lead of said heart monitor.

4. The waveform synchronization system of claim 2, wherein
said each device transmits said one or more packets over said network using a User Datagram Protocol.

5. The waveform synchronization system of claim 1, wherein
said sequence number has an associated bit length;
said sequence number minimum value is zero;
said sequence number maximum value is two raised to a power of a bit width, minus one; and,
said sequence number period is two raised to the power of said bit width.

6. The waveform synchronization system of claim 1, wherein said calculate said unwrapped sequence number for each augmented packet of said one or more augmented packets corresponding to said multiple sampling cycles comprises
calculate a linear mapping from said received timestamp to a predicted approximate unwrapped sequence number; and,
calculate said unwrapped sequence number as a number differing from said sequence number associated with said each augmented packet by an integral multiple of said sequence number period that is closest to said linear mapping applied to said received timestamp associated with said each augmented packet.

7. The waveform synchronization system of claim 1, wherein said calculate said linear relationship between said unwrapped sequence number and said received timestamp comprises
calculate a linear regression between said received timestamp and said unwrapped sequence number for said one or more augmented packets corresponding to said multiple sampling cycles.

8. The waveform synchronization system of claim 1, wherein said calculate said linear relationship between said unwrapped sequence number and said received timestamp comprises
calculate said linear relationship as a line through the received timestamp and unwrapped sequence number of a first augmented packet of said one or more augmented packets having a lowest received timestamp.

9. The waveform synchronization system of claim 8, wherein said calculate said linear relationship between said unwrapped sequence number and said received timestamp further comprises
calculate said linear relationship as said line also through the received timestamp and unwrapped sequence number of a second augmented packet of said one or more augmented packets having a highest received timestamp.

10. The waveform synchronization system of claim 8, wherein said calculate said linear relationship between said unwrapped sequence number and said received timestamp further comprises
calculate said linear relationship as said line also having a slope equal to said same sampling period.

11. The waveform synchronization system of claim 1, wherein
said one or more devices comprises
a first device; and
a second device; and,
said one or more processors comprise one or more inter-device synchronizing processors, wherein said one or more inter-device synchronizing processors are configured to synchronize said synchronized data associated with said first device and said synchronized data associated with said second device.

12. The waveform synchronization system of claim 11, wherein said synchronize said synchronized data associated with said first device and said synchronized data associated with said second device comprises:
calculate a first device adjusted time bias comprising said average difference between the adjusted timestamp and the received timestamp associated with said synchronized data associated with said first device;
calculate a second device adjusted time bias comprising said average difference between the adjusted timestamp and the received timestamp associated with said synchronized data associated with said first device;
subtract said first device adjusted time bias from said adjusted timestamp associated with said synchronized data associated with said first device; and,
subtract said second device adjusted time bias from said adjusted timestamp associated with said synchronized data associated with said second device.

13. The waveform synchronization system of claim 11, wherein said synchronize said synchronized data associated with said first device and said synchronized data associated with said second device comprises:
calculate a cross correlation at a series of time offsets between
said synchronized data associated with said first device; and
said synchronized data associated with said second device, offset in time by each time offset of said series of time offsets;
calculate a phase offset as a time offset corresponding to a maximum value of said cross correlation; and,
subtract set phase offset from said adjusted timestamp associated with said synchronized data associated with said second device.

14. The waveform synchronization system of claim 1, further comprising a database; and,
one or more data storage processors of said one or more processors, said one or more data storage processors configured to
calculate an index associated with each augmented packet of said one or more augmented packets corresponding to said multiple sampling cycles; and,
store said index and said each augmented packet in said database.

15. The waveform synchronization system of claim 14, wherein said calculate said index comprises
calculate a date-time prefix based on said adjusted timestamp of said each augmented packet;
calculate a hash code based on one or more fields of said each augmented packet; and,
calculate said index as a concatenation of said date-time prefix and said hash code.

16. The waveform synchronization system of claim 15, wherein said date-time prefix comprises all or a portion of a Portable Operating System Interface (POSIX) time code.

17. A waveform synchronization system for data received from a network, comprising: one or more processors coupled to the network that is coupled to one or more devices, wherein
- each device of said one or more devices repeatedly samples data from one or more sensors over a time interval comprising multiple sampling cycles, each sampling cycle of said multiple sampling cycles comprising a duration of substantially a same sampling period;
- said each device assigns a sequence number to each of said multiple sampling cycles,
- wherein
- said sequence number is in a range between a sequence number minimum value and a sequence number maximum value;
- said sequence number assigned to a second sampling cycle of said multiple sampling cycles that is immediately after a first sampling cycle of said multiple sampling cycles equals said sequence number assigned to said first sampling cycle plus an increment;
- when said each device increments said sequence number maximum value, said sequence number becomes said sequence number minimum value; and
- said each device comprises a sequence number period equal to a number of distinct sequence numbers between said sequence number minimum value and said sequence number maximum value;
- said sequence number has an associated bit length;
- said sequence number minimum value is zero;
- said sequence number maximum value is two raised to a power of a bit width minus one; and
- said sequence number period is two raised to the power of said bit width;
- said each device transmits over said network one or more packets corresponding to sampled data from said each sampling cycle, wherein
- each packet of said one or more packets comprises
- said sequence number corresponding to said each sampling cycle; and,
- said data from one or more of said one or more sensors that is sampled during said each sampling cycle; and
- said each device transmits said one or more packets over said network using a User Datagram Protocol;
- one or more receiving processors of said one or more processors are configured to receive said one or more packets from said network and to add a received timestamp to said one or more packets to form a corresponding one or more augmented packets;
- said configured to
- delay transmission of any of said one or more packets;
- reorder any of said one or more packets; and,
- lose any of said one or more packets; and,
- one or more synchronizing processors of said one or more processors are configured to receive said one or more augmented packets corresponding to said multiple sampling cycles;
- calculate an unwrapped sequence number for each of said one or more augmented packets corresponding to said multiple sampling cycles, wherein
- said unwrapped sequence number uniquely identifies each of said multiple sampling cycles;
- said calculate said unwrapped sequence number for each augmented packet of said one or more augmented packets corresponding to said multiple sampling cycles comprises
- calculate a linear mapping from said received timestamp to a predicted approximate unwrapped sequence number; and,
- calculate said unwrapped sequence number as a number differing from said sequence number associated with said each augmented packet by an integral multiple of said sequence number period that is closest to said linear mapping applied to said received timestamp associated with said each augmented packet;
- calculate a linear relationship between said unwrapped sequence number and said received timestamp for said one or more augmented packets corresponding to said multiple sampling cycles as a linear regression between said received timestamp and said unwrapped sequence number for said one or more augmented packets corresponding to said multiple sampling cycles;
- apply said linear relationship to said unwrapped sequence number of said one or more augmented packets corresponding to said multiple sampling cycles to obtain an adjusted timestamp of each of said one or more augmented packets; and,
- synchronize said data across said one or more sensors over said time interval based on said adjusted timestamp to form synchronized data associated with said each device.

18. The waveform synchronization system of claim 17, wherein
- said one or more devices comprises
- a first device; and
- a second device; and,
- said one or more processors comprise one or more inter-device synchronizing processors, wherein said one or more inter-device synchronizing processors are configured to synchronize said synchronized data associated with said first device and said synchronized data associated with said second device; and,
- said synchronize said synchronized data associated with said first device and said synchronized data associated with said second device comprises:
- calculate a first device adjusted time bias comprising an average difference between the adjusted timestamp and the received timestamp associated with said synchronized data associated with said first device;
- calculate a second device adjusted time bias comprising an average difference between the adjusted timestamp and the received timestamp associated with said synchronized data associated with said first device;
- subtract said first device adjusted time bias from said adjusted timestamp associated with said synchronized data associated with said first device; and,
- subtract said second device adjusted time bias from said adjusted timestamp associated with said synchronized data associated with said second device.

19. The waveform synchronization system of claim 18, further comprising a database; and,
- one or more data storage processors of said one or more processors, said one or more data storage processors configured to
- calculate an index associated with each augmented packet of said one or more augmented packets corresponding to said multiple sampling cycles; and, store said index and said each augmented packet in said database;

wherein said calculate said index comprises calculate a date-time prefix based on said adjusted timestamp of said each augmented packet;

calculate a hash code based on one or more fields of said each augmented packet; and, calculate said index as a concatenation of said date-time prefix and said hash code.

20. The waveform synchronization system of claim 19, wherein said date-time prefix comprises all or a portion of a Portable Operating System Interface (POSIX) time code.

* * * * *

UNITED STATES PATENT AND TRADEMARK OFFICE
CERTIFICATE OF CORRECTION

| | | |
|---|---|---|
| PATENT NO. | : 11,496,232 B1 | Page 1 of 1 |
| APPLICATION NO. | : 17/306864 | |
| DATED | : November 8, 2022 | |
| INVENTOR(S) | : Harsh Dharwad et al. | |

It is certified that error appears in the above-identified patent and that said Letters Patent is hereby corrected as shown below:

On the Title Page

Item (72) In the Inventors:
Replace "Timoty Ruchti, Gurnee (CA)" with --Timothy Ruchti, Gurnee, IL (US)--.

Signed and Sealed this
Eleventh Day of June, 2024

Katherine Kelly Vidal
*Director of the United States Patent and Trademark Office*